(12) United States Patent
Shapiro et al.

(10) Patent No.: US 9,108,035 B2
(45) Date of Patent: *Aug. 18, 2015

(54) METHODS AND SYSTEMS FOR USING THERAPEUTIC, DIAGNOSTIC OR PROPHYLACTIC MAGNETIC AGENTS

(71) Applicants: University of Maryland College Park, College Park, MD (US); The Government of the United States of America, as represented by the Department of Health and Human Services, Washington, DC (US)

(72) Inventors: Benjamin Shapiro, Washington, DC (US); Michael R. Emmert-Buck, Easton, MD (US)

(73) Assignees: University of Maryland, College Park, College Park, MD (US); The United States of America as represented by the Secretary, Department of Health and Human Services, National Institutes of Health, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/075,408

(22) Filed: Nov. 8, 2013

(65) Prior Publication Data
US 2014/0066752 A1 Mar. 6, 2014

Related U.S. Application Data

(63) Continuation of application No. 12/468,746, filed on May 19, 2009, now Pat. No. 8,579,787.

(60) Provisional application No. 61/054,239, filed on May 19, 2008.

(51) Int. Cl.
*A61N 2/00* (2006.01)
*A61N 2/02* (2006.01)
(Continued)

(52) U.S. Cl.
CPC . *A61N 2/00* (2013.01); *A61B 5/055* (2013.01); *A61N 2/02* (2013.01); *A61N 2/06* (2013.01); *A61N 1/406* (2013.01)

(58) Field of Classification Search
CPC ............. A61N 2/00; A61N 2/02; A61N 2/06; A61N 5/055
USPC ................................. 600/9–15; 128/897–899
See application file for complete search history.

(56) References Cited

U.S. PATENT DOCUMENTS 4,662,359 A 5/1987 Gordon
4,690,130 A 9/1987 Mirell
(Continued)

FOREIGN PATENT DOCUMENTS

WO WO 03007996 1/2003
WO WO 03022360 3/2003
(Continued)

OTHER PUBLICATIONS

Avilés, M.O. et al. (2005) "Theoretical Analysis of a Transdermal Ferromagnetic Implant for Retention of Magnetic Drug Carrier Particles," J. Magnetism and Magnetic Materials 293:605-615.
(Continued)

*Primary Examiner* — John Lacyk
(74) *Attorney, Agent, or Firm* — William C. Schrot; AuerbachSchrot LLC

(57) ABSTRACT

Systems and methods are disclosed for directing magnetizable particles comprising therapeutic agents to a target volume, or for guiding magnetizable particles comprising therapeutic agents from a first target volume to a second target volume, at a distance using a magnetic field, to enable the treatment of diseased areas including areas deep inside a patient's body. The methods may be used to diagnose or treat diseased areas within a patient, for example tumors of the lungs, intestines, and liver, and is also useful in enhancing the permeability of solid tumors to chemotherapeutic agents.

26 Claims, 16 Drawing Sheets

(51) Int. Cl.
  *A61N 2/06* (2006.01)
  *A61B 5/055* (2006.01)
  *A61N 1/40* (2006.01)

(56) References Cited

U.S. PATENT DOCUMENTS

| | | | |
|---|---|---|---|
| 4,869,247 | A | 9/1989 | Howard, III et al. |
| 5,010,897 | A | 4/1991 | Leveen |
| 5,099,756 | A | 3/1992 | Franconi et al. |
| 5,203,782 | A | 4/1993 | Gudov et al. |
| 5,236,410 | A | 8/1993 | Granov et al. |
| 5,339,347 | A | 8/1994 | Slatkin et al. |
| 5,667,469 | A | 9/1997 | Zhang et al. |
| 5,835,995 | A | 11/1998 | Macovski et al. |
| 5,921,244 | A | 7/1999 | Chen et al. |
| 6,128,174 | A | 10/2000 | Ritter et al. |
| 6,241,671 | B1 | 6/2001 | Ritter et al. |
| 6,245,005 | B1 | 6/2001 | Von Gutfeld et al. |
| 6,296,604 | B1 | 10/2001 | Garibaldi et al. |
| 6,298,259 | B1 | 10/2001 | Kucharczyk et al. |
| 6,315,709 | B1 | 11/2001 | Garibaldi et al. |
| 6,447,999 | B1 | 9/2002 | Giesen et al. |
| 6,470,220 | B1 | 10/2002 | Kraus, Jr. et al. |
| 6,475,223 | B1 | 11/2002 | Werp et al. |
| 6,546,279 | B1 | 4/2003 | Bova et al. |
| 6,776,165 | B2 | 8/2004 | Jin |
| 6,842,324 | B2 | 1/2005 | Eyssa |
| 7,074,175 | B2 | 7/2006 | Handy et al. |
| 7,189,198 | B2 | 3/2007 | Harburn et al. |
| 7,723,311 | B2 | 5/2010 | Seeney et al. |
| 8,579,787 | B2 * | 11/2013 | Shapiro et al. .............. 600/12 |
| 2002/0147424 | A1 | 10/2002 | Ostrow et al. |
| 2003/0073879 | A1 | 4/2003 | Sandstrom |
| 2004/0030244 | A1 | 2/2004 | Garibaldi et al. |
| 2004/0156919 | A1 | 8/2004 | Lee |
| 2005/0019267 | A1 | 1/2005 | Kim et al. |
| 2005/0129727 | A1 | 6/2005 | Weber et al. |
| 2005/0267457 | A1 | 12/2005 | Hruschka |
| 2006/0041182 | A1 | 2/2006 | Forbes et al. |
| 2006/0176997 | A1 | 8/2006 | Dilmanian et al. |
| 2006/0188442 | A1 | 8/2006 | Hallahan |

FOREIGN PATENT DOCUMENTS

| | | |
|---|---|---|
| WO | WO 2005065282 | 7/2005 |
| WO | WO 2007079276 | 7/2007 |
| WO | WO 2007113572 | 10/2007 |
| WO | WO 2009076465 | 6/2009 |

OTHER PUBLICATIONS

Ganguly, R. et al. (2005) "*Analyzing Ferrofluid Transport for Magnetic Drug Targeting,*" J. of Magnetism and Magnetic Materials, 289:331-334.

Grief, A. D. et al. (2005) "*Mathematical Modelling of Magnetically Targeted Drug Delivery,*" J. of Magnetism and Magnetic Materials, 293:455-463.

Hafeli, U. O. et al. (2007) "*Modeling of Magnetic Bandages for Drug Targeting: Button vs. Halbach Arrays,*" J. of Magnetism and Magnetic Materials, 311:323-329.

Iacob, G.H. et al. (2004) "*A Possibility for Local Targeting of Magnetic Carriers,*" J. Optoelectronics and Advanced Materials 6:713-717.

Iacob, G.H. et al. (2004) "*Magnetizable Needles and Wires—Modeling an Efficient Way to Target Magnetic Microspheres in vivo,*" Biorheology 41:599-612.

International Search Report and Written Opinion; PCT/US2008/086276 (WO 2009/076465) (2009)(12 pages).

Earnshaw, S. (1842) "*On the Nature of the Molecular Forces Which Regulate the Constitution of the Luminiferous Ether,*" Trans. Camb. Phil. Soc. 7:97-112.

Kenney, C. J. et al. (2006) "*Active-Edge Planar Radiation Sensors,*" Nuclear Instruments and Methods in Physics Research A, 565:272-277.

Lemke, M. I. et al., (2004) "*MRI After Magnetic Drug Targeting in Patients With Advanced Solid Malignant Tumors,*" Eur. Radiology, 14:1949-1955.

Lubbe, A. S. et al. (1996) "*Clinical Experiences With Magnetic Drag Targeting: A Phase I Study With 4'-Epidoxorubicin in 14 Patients With Advanced Solid Tumors,*" Cancer Res., 56:4686-4693.

Lubbe, A. S. et al. (1996) "*Preclinical Experiences With Magnetic Drug Targeting: Tolerance and Efficacy,*" Cancer Res., 56:4694-4701.

Martel, S. et al. (2007) "*Automatic Navigation of an Untethered Device in the Artery of a Living Animal Using a Conventional Clinical Magnetic Resonance Imaging System,*" Applied Physics Letters 90:114105.

Mathieu, J. B. et al. (2007) "*Magnetic Microparticle Steering Within the Constraints of an MRI System: Proof of Concept of a Novel Targeting Approach,*" Biomedical Microdevices, 9:801-808.

Parker, S. I. et al. (2006) "*3DX: An X-Ray Pixel Array Detector With Active Edges,*" IEEE Transactions on Nuclear Science, 53:1676-1688.

Potts, H. E. et al. (2001) "*Dynamics of Freely-Suspended Drops,*" J. of Physics D-Applied Physics, 34:2629-2636.

Rosengart, A.J. et al. (2005) "*Magnetizable Implants and Functionalized Magnetic Carriers: A Novel Approach for Noninvasive Yet Targeted Drug Delivery,*" J. Magnetism and Magnetic Materials 293:633-638.

Ritter, J.A. et al. (2004) "*Application of High Gradient Magnetic Separation Principles to Magnetic Drug Targeting,*" J. Magnetism and Magnetic Materials, 280:184-201 (2004).

Rotariu, O. et al. (2005) "*Modelling Magnetic Carrier Particle Targeting in the Tumor Microvasculature for Cancer Treatment,*" J. Magnetism and Magnetic Materials, 293:639-647.

Shapiro, B. (2009) "Towards dynamic control of magnetic fields to focus magnetic carriers to targets deep inside the body," J. Magn. Magn. Mater. 321(10):1594; pp. 1-13.

Voltairas, P. A. et al. (2002) "*Hydrodynamics of Magnetic Drug Targeting,*" Journal of Biomechanics, 35: 813-821.

Yellen, B.B. et al. (2005) "*Targeted Drug Delivery to Magnetic Implants for Therapeutic Applications,*" J. Magnetism and Magnetic Materials, 293:647-654.

Laura Elena Udrea, Norval J C Strachan, Vasile Badescu and Ovidiu Rotariu, An in vitro study of magnetic particle targeting in small blood vessels, Phys. Med. Biol. 51 (2006) pp. 4869-4881.

UB News Direct Online "Magnetic Field Acts as Remote Control to Delivery Nanomedicine", Jun. 6, 2006, pp. 1-3.

U.O. Hafeli, "Magnetically modulated therapeutic systems", International Journal of Pharmaceutics 277 (2004), pp. 19-24.

E.P. Furlani and K.C. NG, "Analytical model of magnetic nanoparticle transport and capture in the microvasculature", Institute for Lasers, Photonics and Biophotonics, University of Buffalo, Buffalo, New York 14260, Jun. 27, 2006 pp. 061919-1-061919-10.

Sally J. Denardo, et al, Development of Tumor Targeting Bioprobes (In-Chimeric L6 Monoclonal Antibody Nanoparticles) for Alternating Magnetic Field Cancer Therapy, Oct. 1, 2005 pp. 1-6.

H.E. Potts and D.A. Diver, Ferrofluid Hydrodynamics: waves, Jets and Free Drops, Dept of Physics and Astronomy, University of Glasgow, Scotland UK, Jan. 17, 2001, pp. 1-8.

Christoph Alexiou et al, Targeting cancer cells: magnetic nanoparticles as drug carriers, Biophysics Letter, (2006), pp. 446-450.

* cited by examiner

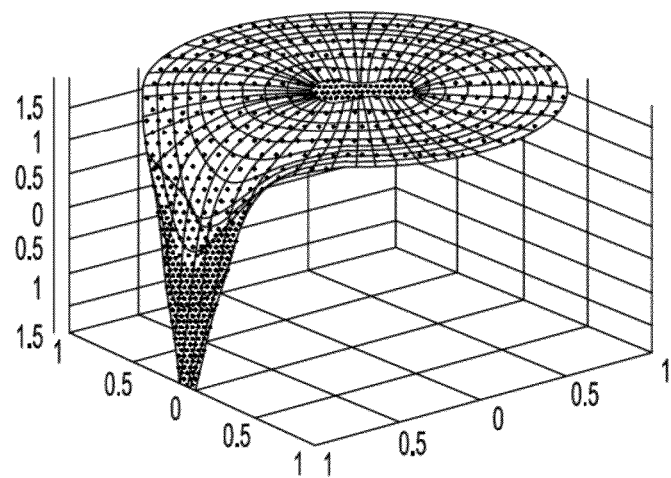
FIG.8A
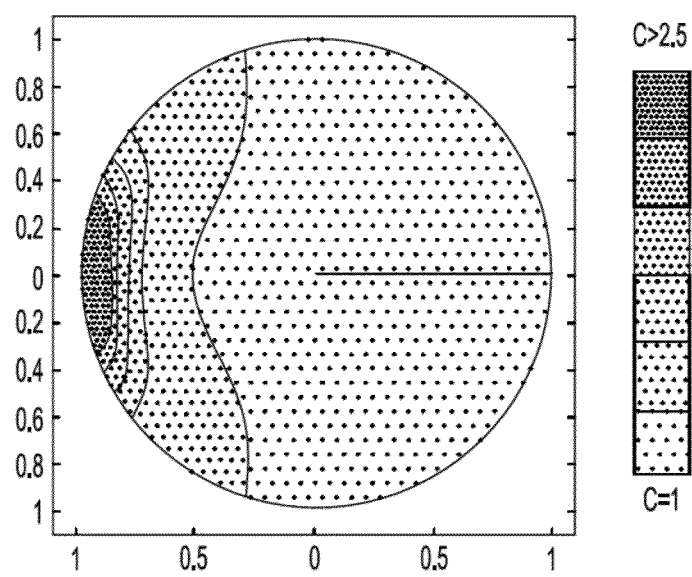
FIG.8Aii

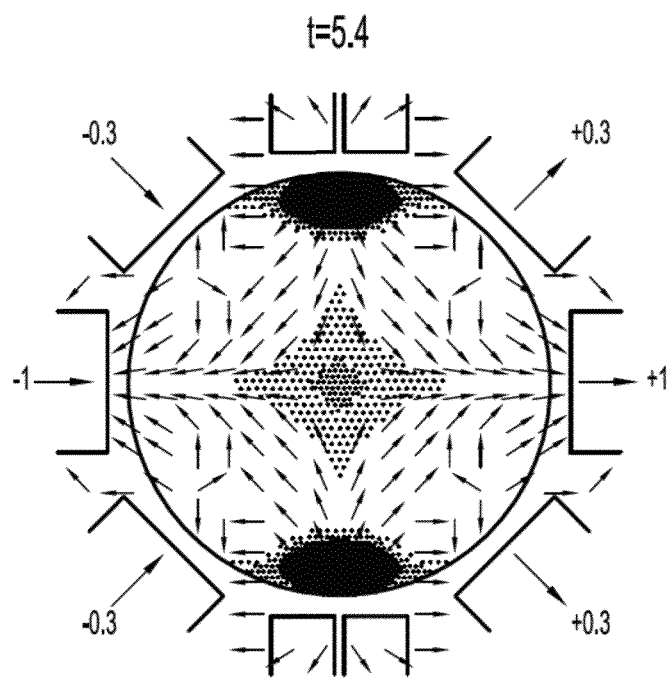
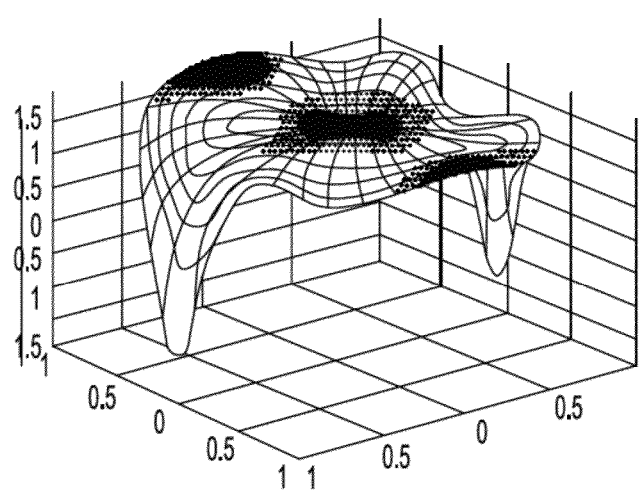
FIG.8Bii

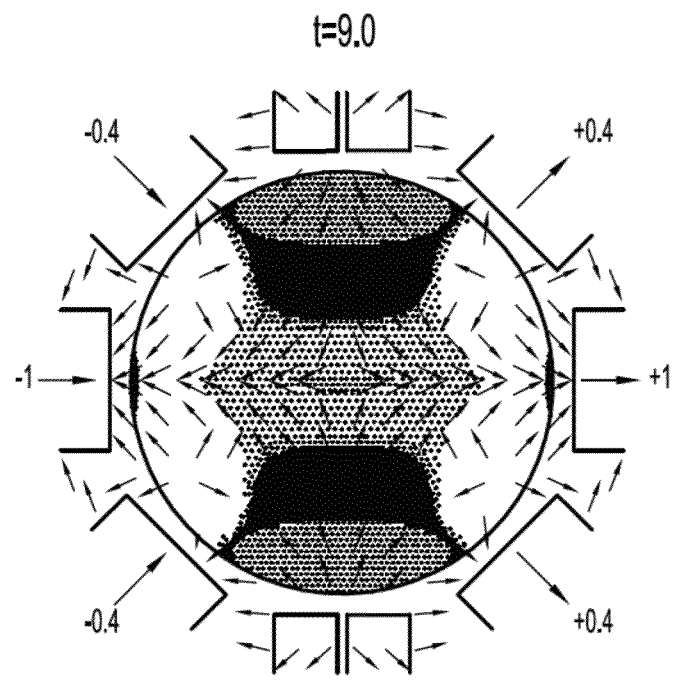
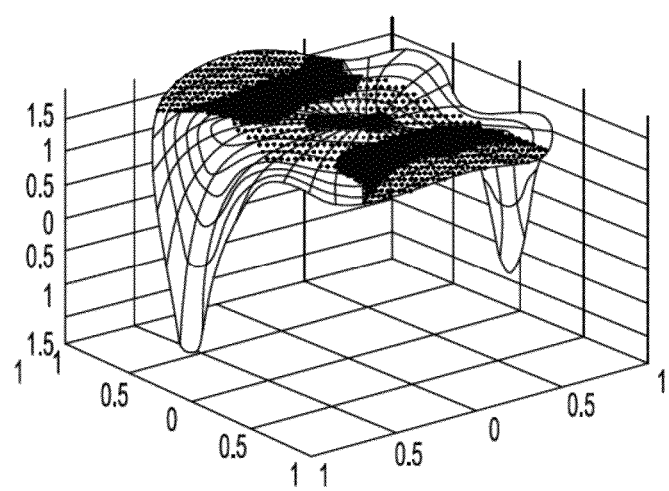
FIG.8Biii

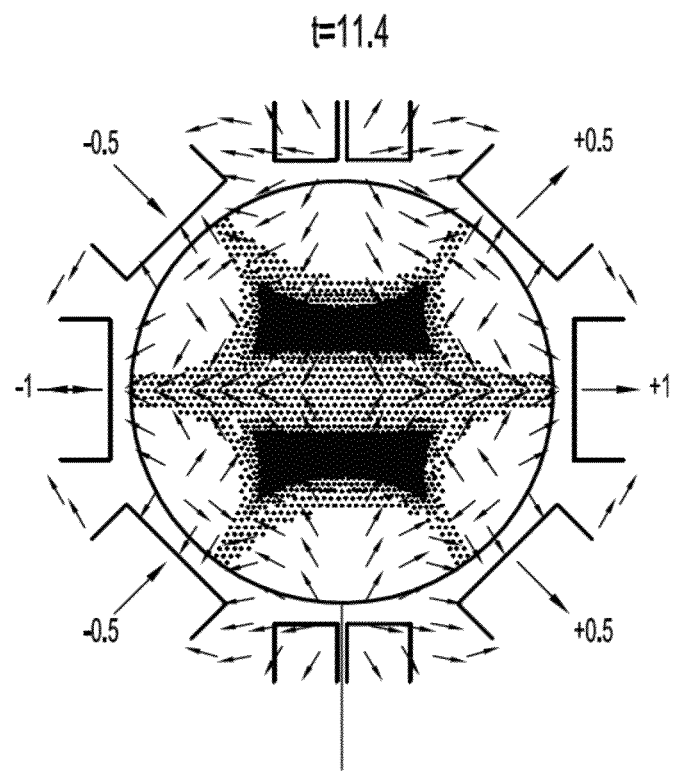
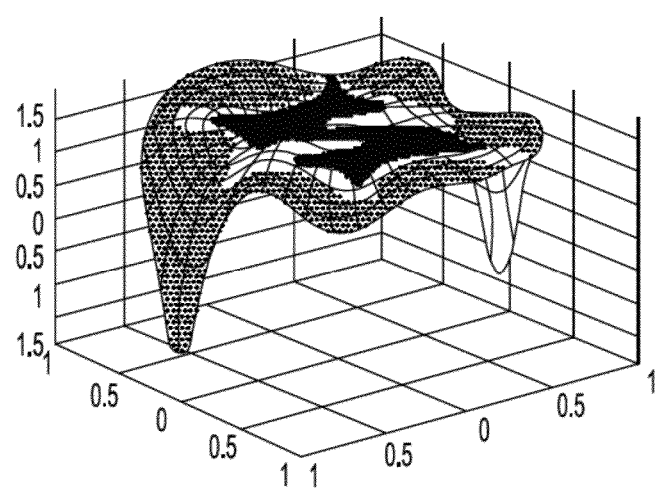
FIG.8Biv

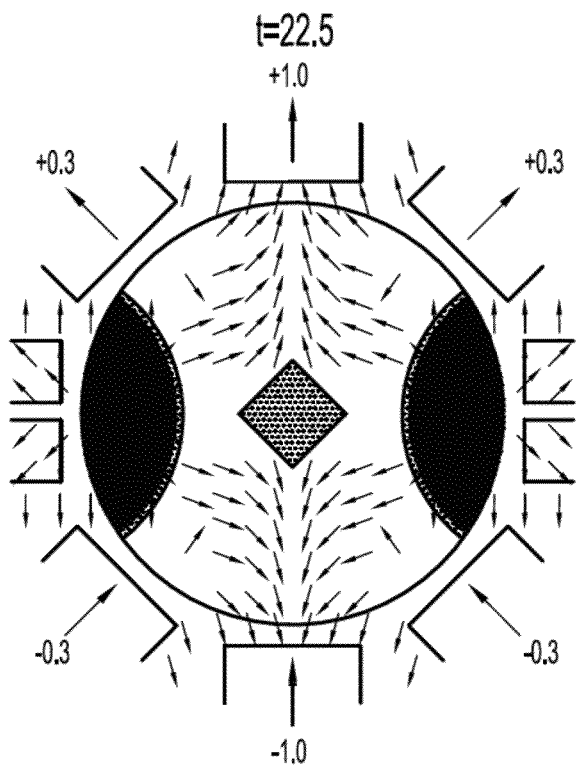
FIG.8Bvi
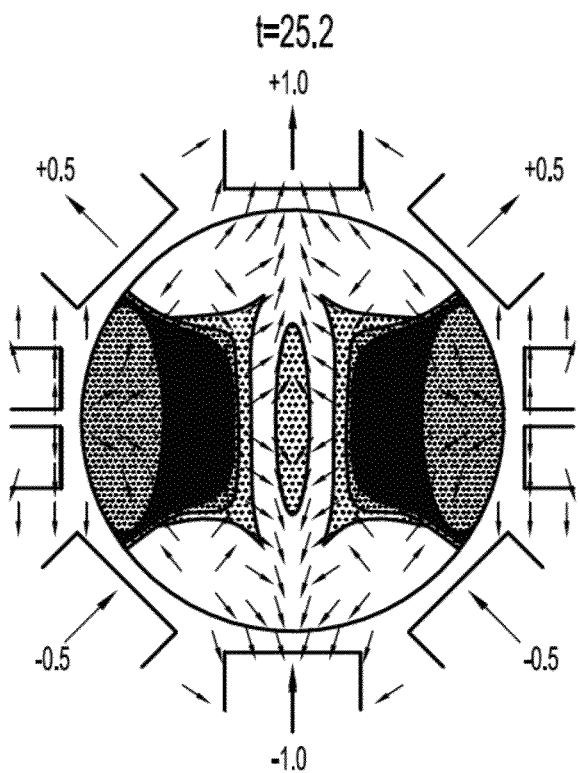
FIG.8Bvii

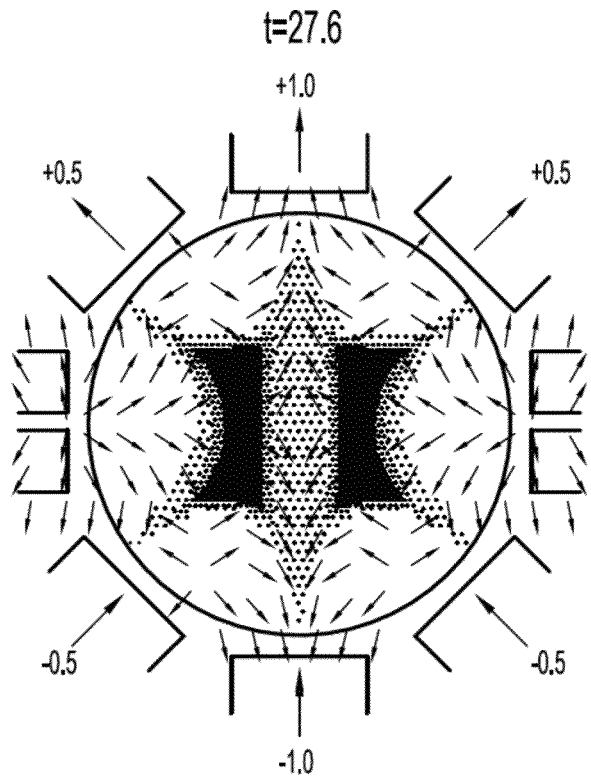
FIG.8Bviii
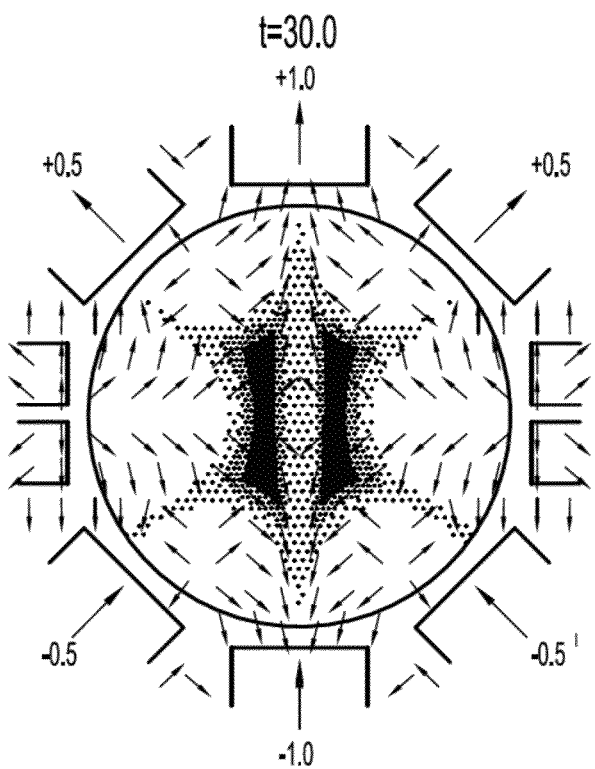
FIG.8Bix

METHODS AND SYSTEMS FOR USING THERAPEUTIC, DIAGNOSTIC OR PROPHYLACTIC MAGNETIC AGENTS

CROSS-REFERENCE TO RELATED APPLICATIONS

This application is a continuation of U.S. patent application Ser. No. 12/468,746, filed on May 19, 2009, which application is based on U.S. Provisional Patent Application No. 61/054,239, filed on May 19, 2008, which applications are all incorporated herein by reference in their entireties and to which priority is claimed.

STATEMENT REGARDING FEDERALLY-SPONSORED RESEARCH

This invention was made with government support under the Intramural Program of the National Cancer Institute, National Institutes of Health. The government has certain rights in the invention.

BACKGROUND OF THE INVENTION

1. Field of the Invention

This invention relates generally to magnetic therapeutic systems and methods, and specifically, to systems and methods for using magnetic fields to contain magnetizable therapeutic, diagnostic or prophylactic agents in a target volume within a patient's body, or to move such magnetizable agents through a target volume within a patient's body.

2. Description of Related Art

Cancer is a major cause of death in the United States, claiming more than 500,000 lives each year according to American Cancer Society estimates. The primary treatment options for cancer are surgery, radiation therapy, chemotherapy, and immunotherapy. Although surgical removal of a primary tumor is usually the favored option, some tumors are inoperable, for example because they are inaccessible or have ill-defined borders. Thus, radiation therapy, chemotherapy, and immunotherapy are often used to treat cancer in conjunction with, or instead of, surgery. In later (metastatic) stages of disease, the patient can have multiple metastatic tumor foci that range in size from microscopic to grossly visible, and includes metastases in unknown anatomical locations. In these cases one-by-one removal of tumors is not feasible and thus surgery is not an effective clinical strategy. For patients with metastatic disease, radiation therapy to regions of the body that contain large/detectable metastic tumors, systemic chemotherapy, and immunotherapy are the usual remaining options.

Radiation therapy, chemotherapy, and immunotherapy can achieve some success in treating cancer, but these treatments have disadvantages as well. For example, radiation therapy usually treats only a specific small region of the body and there may be metastatic tumors outside this region. Moreover, hypoxic cancer cells in solid tumors are less prone to the DNA damage caused by radiation, and therefore can be resistant to radiation therapy. Immunotherapy also has disadvantages, in that non-tumor cells can be damaged by the treatment, delivery to tumor cells may be inefficient, clinical efficacy may be low, and toxicity may be unacceptably high. Chemotherapy remains a primary treatment for cancer, but also has disadvantages, including poor delivery and cellular uptake of chemotherapeutic agents into malignant tissue, drug resistance and non-specific toxicity. Further, the dosage of chemotherapeutic agents is usually limited to a dosage that the patient can withstand, however such a dosage may not be high enough to effectively treat all or even the majority of malignant cells.

Poor delivery of therapeutic agents to diseased cells is a difficult problem in cancer treatment, especially treatment of cancers that have spread widely, including lesions that are deep within the body. Even when the agents are delivered to the locale of a tumor mass, poor penetrability into the tumor mass may require prolonged high dose treatment, and subsequent severe systemic adverse effects. For these reasons, it is desirable to provide improved and alternative techniques for treating disease, particularly techniques that are less invasive and traumatic to the patient than those currently in practice. The promise of targeted drug delivery is that therapeutic agents can be targeted to diseased tissue, thereby enabling high concentrations in tumors, with lower concentrations elsewhere in the body. This promise can be effected by targeting a specific region or volume in the patient that likely contains the majority of cancer metastases that would cause morbidity and mortality if left unchecked, but whose specific location, number, and properties are not known in detail. For example, it is known that breast cancer usually metastasizes to the lungs and liver, thus an ability to confine chemotherapy to the upper torso would likely provide improved clinical efficacy while minimizing the side-effects of chemotherapy in the rest of body (for example, sparing the immune system and bone marrow in regions outside the upper torso). In many cancers, such a treatment could address the majority of clinically relevant tumors. Although it would not eliminate the entire tumor burden in a patient it would effectively treat the most clinically problematic tumor foci and thereby change the disease from a death sentence into a chronic, manageable condition. Such targeted drug delivery to specific anatomical regions of the body is thus potentially valuable but has not been achieved using current targeted delivery techniques; methods and systems to achieve this goal are the subject of the current patent.

The ability to focus therapeutic agents to specific locations is useful not only for cancer treatment, but also for the treatment of diseases or disorders that are localized in the body, for example a localized infection such as a spinal abscess, or as a second example, restenosis in a coronary artery. Targeted delivery techniques are being explored for the treatment of cancers and other diseases, and include three primary approaches: passive targeting, active targeting, and physical targeting. Passive targeting techniques rely on selective accumulation of drugs at the tumor site due to differences between healthy and tumor cells, for example the Enhanced Permeability and Retention (EPR) effect, or on localized delivery, for example direct intratumoral delivery in prostate cancer treatment. Active targeting techniques include conjugating the therapeutic agent to a targeting ligand, such as RGD peptides, and tumor-specific antibodies. Physical targeting techniques include stimulating target tumor tissue with ultrasonic waves, which promotes intracellular drug uptake.

Magnetic drug delivery has also been attempted, in which drugs are attached to magnetic particles, and then magnetic fields from stationary magnets outside the body are used to focus the drugs to specific locations near the surface of the body. Magnetic drug particles for treatment of shallow tumors have been tested for safety and efficacy in animal and human clinical trials, where particles are injected into a vein, distributed throughout the body by the circulatory system, and then captured and concentrated at the desired shallow tumor location by a strong stationary magnet held near the tumor. Direct injection of magnetic particles into a tumor, followed by thermal excitation of the magnetic particles, has also been attempted with some success in the treatment of prostate cancers. However, non-invasive magnetic drug delivery to deep tissue such as the lungs, intestines, and liver, has not been successful because the magnetic fields necessary to overcome blood flow rates in the arteries, and to target the nanoparticles more than about 5 centimeters inside the body, generally exceed the threshold (~1-8 Tesla) of what is considered safe for human application. Thus, conventional magnetic drug targeting has not proven successful with deep tissue tumors. The above depth limit also means that it is not currently possible to magnetically confine treatment to a desired target volume that includes deep regions. For example, it is not possible to confine drugs to the entirety of the lungs, liver, or upper torso including its deep-in-the-body portions. Thus current magnetic drug delivery cannot focus treatment to the majority of cancer metastases that will cause morbidity and mortality if left untreated and whose numbers, properties, and anatomic locations are unknown but are still often largely confined to a specific volume of the body (even in late and advanced stages of the disease).

What is needed are improved magnetic drug delivery methods and systems that overcome these difficulties and results in improved therapeutic, diagnostic or prophylactic use of magnetic agents, particularly for treatment of desired target volumes that include deep regions and many hard to access metastatic tumors whose exact location is not known.

SUMMARY OF THE INVENTION

The present invention relates to methods and systems for containment of therapeutic, diagnostic or prophylactic agents to a target volume within a patient using magnetic fields, and also relates to methods and systems for moving therapeutic, diagnostic or prophylactic agents through a target volume (to better reach many hard to access metastases) within a patient using magnetic fields. The invention includes methods and systems grouped into two basic approaches: regional targeting, and sweeping.

In regional targeting, magnetic fields are shaped, in space, time, or both, to direct therapeutic, diagnostic or prophylactic magnetizable objects to a region of the body, such as, for example, the upper torso for breast cancer patients. By primarily confining treatment to this anatomical region, chemotherapy or other cancer treatments can be targeted to all metastases in that region while sparing cells in the rest of the body. This can address the majority of clinically relevant tumors, those tumors that if left unchecked will cause morbidity and mortality. It does not require exact knowledge of tumor locations (in the breast cancer example, it is known that the majority of clinically relevant metastases will be found in the upper torso, e.g. in the lungs and liver, and all these tumors will be treated). It does not require a one-by-one treatment of tumors which is usually not feasible since advanced cancer patients can have thousands of metastatic foci. Yet it still spares the rest of the patient's body (in the breast cancer example bone marrow and the immune system are spared in the lower torso, arms, legs, and head).

In sweeping, magnetizable objects are swept through a region or regions to better target hard to reach metastases. Even if therapy can be confined to a specific anatomical region (such as the upper torso or the liver) it is still possible that the metastases within this region are hard to access and therapeutic delivery to them will be poor. For example, based on results from autopsies we have carried out at the National Cancer Institute, and contrary to the accepted dogma that metastases typically recruit blood vessels and are therefore well vascularized, we have found that metastases in patients with late stage disease often have a poor blood supply. This means that it is hard to access these tumors by magnetizable objects distributed into the blood (the usual magnetic drug delivery approach). By delivering the magnetizable objects to a volume that surrounds, is in direct contact with, or is otherwise linked to metastases, we can then use the magnetic field to sweep magnetizable objects from the first volume to the poorly-vascularized metastases, thus potentially dramatically improving therapeutic efficacy. Moreover, similar to the regional drug targeting described above, the sweeping approach can be successfully employed without knowledge of the anatomical location of the metastases as all lesions can be treated simultaneously by sequentially altering the magnetic fields to drive the particles in different coordinate planes.

The methods and systems can further comprise detecting at least one location of the plurality of magnetizable objects within the patient, and using a feedback controller to control at least one externally applied magnetic field in response to said detection. This sensing and feedback allows better control of delivery to desired target volumes and more efficacious choice of directions to sweep. Thus methods and systems for treating a patient are provided, which comprise administering a plurality of magnetizable objects to a patient and externally applying shaped magnetic fields to the patient in order to contain the plurality of magnetizable objects within a target volume within the patient, and/or, to sweep the objects from a first region or volume to second volumes that contain hard to access metastatic tumors.

The present invention relates to methods and systems for directing therapeutic, diagnostic or prophylactic agents to a target volume within a patient using magnetic fields, and also relates to methods and systems for directing therapeutic, diagnostic or prophylactic agents from a first target volume to one or more second target volumes within a patient using magnetic fields. The methods and systems can further comprise detecting at least one location of the plurality of magnetizable objects within the patient, and using a feedback controller to control at least one externally applied magnetic field in response to said detection. Methods and systems for treating a patient are provided, which comprise administering a plurality of magnetizable objects to a patient and externally applying a magnetic field to the patient in order to direct the plurality of magnetizable objects to a target volume within the patient.

Also provided are methods and systems for treating a patient comprising the steps of administering a plurality of magnetizable objects to a patient, and externally applying a shaped magnetic field to the patient in order to direct the plurality of magnetizable objects to a first desired target volume within the patient. The magnetic field can be a shaped dynamic magnetic field, which may have a rate of change of up to about 20 Tesla/second. The magnetic field can be a shaped static magnetic field. The magnetic field can be a shaped internally applied magnetic field, which can be applied by at least one implanted magnet. The magnetic field can be a shaped externally and internally applied magnetic field. In the methods, the effectiveness of the directing can be measured over a period of time. The first desired target volume can be composed of multiple desired sub-volumes. The application of the shaped magnetic field can direct the plurality of magnetizable objects to the desired target volume, or can expel or prevent the plurality of magnetizable objects from remaining outside the desired target volume.

The target volume can be associated with a cancer, a disease of the vascular system, a disease of an organ, an infection, or non-cancerous disease material, and can be associated with metastasized cancer. The first desired target volume can be selected to contain at least one primary tumor, at least one metastatic tumor, at least one infectious lesion, at least one infectious organism, at least one blood clot, or at least one diseased biological structure. The first desired target volume can be selected to contain at least one individual organ, an organ system, or a specific anatomic region, and the organ system can be selected from the group consisting of the circulatory system, the gastrointestinal tract, the genitourinary tract, the pulmonary system, and the dermal system. The first desired target volume can contain multiple metastatic tumors or tumor cells. The first desired target volume can contain multiple infectious lesions, multiple infectious organisms, multiple blood clots, or multiple diseased biological structures, and the first desired target volume can be selected based on the anatomical region in which the multiple infectious lesions, multiple infectious organisms, multiple blood clots, or the multiple diseased biological structures are suspected to be located. The location of at least some of the multiple infectious lesions, multiple infectious organisms, multiple blood clots, or the multiple diseased biological structures can be undetectable via conventional diagnostic means. The first desired target volume can be selected to contain multiple clinically significant metastases suspected to be in a particular anatomical region, and the location of at least some of the clinically significant metastases can be undetectable via conventional diagnostic means. At least one part of the first target volume can be located at least 5 centimeters inside the patient.

Further provided are methods and systems for treating a patient comprising the steps of administering a plurality of magnetizable objects to a patient, directing the plurality of magnetizable objects to a first desired target volume within the patient, and directing the plurality of magnetizable objects to a second desired target volume within the patient, wherein at least one of said directing steps comprises externally applying a shaped magnetic field to the patient in order to direct the plurality of magnetizable objects. In certain methods and systems, the step of directing the plurality of magnetizable objects to the first desired target volume within the patient comprises externally applying a shaped magnetic field to the patient in order to direct the plurality of magnetizable objects to the first desired target volume, and the step of directing the plurality of magnetizable objects to the second desired target volume within the patient comprises non-magnetic means of directing the plurality of magnetizable objects to the second desired target volume. In other methods and systems, the step of directing the plurality of magnetizable objects to the first desired target volume within the patient comprises non-magnetic means of directing the plurality of magnetizable objects to the first desired target volume, and the step of directing the plurality of magnetizable objects to the second desired target volume within the patient comprises externally applying a shaped magnetic field to the patient in order to direct the plurality of magnetizable objects to the second desired target volume. In still other methods and systems, both of the directing steps can comprise externally applying a shaped magnetic field to the patient in order to direct the plurality of magnetizable objects.

The non-magnetic means can comprise electrical, thermal, mechanical, chemical or biological means, and the biological means can comprise passive diffusion, extravasation, or active transport, or a combination thereof. The magnetic field can be a shaped dynamic magnetic field, which may have a rate of change of up to about 20 Tesla/second. The magnetic field can be a shaped static magnetic field. The magnetic field can be a shaped internally applied magnetic field, which can be applied by at least one implanted magnet. The magnetic field can be a shaped externally and internally applied magnetic field. In the methods, the effectiveness of the directing can be measured over a period of time. The first desired target volume can be composed of multiple desired sub-volumes.

The second desired target volume can be selected from the group consisting of a primary tumor, a metastatic tumor, an infectious lesion, an infectious organism, a blood clot, and a diseased biological structure, and the second desired target volume is different than the first desired target volume. The second desired target volume can be selected from the group consisting of an individual organ, an organ system, and a specific anatomic region, and the second desired target volume is different than the first desired target volume. The second desired target volume can be associated with a cancer, a disease of the vascular system, a disease of an organ, an infection, or non-cancerous disease material. The second desired target volume can be associated with metastasized cancer. The second desired target volume can be composed of multiple desired sub-volumes. The second target volume can contain, or be composed of, multiple metastatic tumors or tumor cells, and the second desired target volume can be selected to contain multiple clinically significant metastases made accessible by the first volume. The location of at least some of the clinically significant metastases can be undetectable via conventional diagnostic means. The second volume can be composed of metastatic tumors and cells that are poorly vascularized and cannot be readily accessed by blood flow.

The second target volume can contain, or be composed of, multiple infectious lesions, multiple infection organisms, multiple blood clots, or multiple diseased biological structures. The second target volume can be difficult to access and can only be practically reached by first directing the magnetizable objects to the first volume which then provides better access to the target second volume. The first volume can surround, be in contact with, be near, or be linked by the vasculature, lymphatic, intestinal, interstitial, or cellular transport systems, to the desired target second volume. The application of the shaped magnetic field can direct the plurality of magnetizable objects to the desired target volume, or can expel or prevent the plurality of magnetizable objects from remaining outside the desired target volume. The methods and systems can further comprise causing the plurality of magnetizable objects to move from the at least one second desired target volume back to the first desired target volume, or causing the plurality of magnetizable objects to move from the at least one second desired target volume to at least one third desired target volume.

Other methods and systems are provided for treating a patient comprising the steps of administering a plurality of magnetizable objects to a patient, accumulating the plurality of magnetizable objects in a first desired target volume within the patient, externally applying a shaped magnetic field to the patient in order to cause the plurality of magnetizable objects to move from the first desired target volume to a second desired target volume within the patient, and externally applying a shaped magnetic field to the patient in order to cause the plurality of magnetizable objects to move from the second desired target volume back to the first desired target volume. The methods and systems can further comprise externally applying a shaped magnetic field to the patient in order to cause the plurality of magnetizable objects to move from the first desirable target volume to a third desirable target volume and back to the first desirable target volume. The methods and systems can further comprise externally applying a shaped magnetic field to the patient in order to cause the plurality of magnetizable objects to move through a sequence of volumes surrounding the second target volume on all or a majority of sides. The methods and systems can further comprise directing the plurality of magnetizable objects from the subsequent volumes to the target second volume from a sequence of directions so that all or a majority of parts of the second volume may be accessed efficaciously.

The magnetizable objects can be between about 1 μm and 1 mm in diameter, or between about 1 μm and 1 nm in diameter. The plurality of magnetizable objects can comprise a magnetizable component of a ferrofluid, and can comprise a therapeutic, diagnostic or prophylactic agent. The magnetizable objects can comprise a detectable label, which can be a radioisotopic label, a paramagnetic label, a CARS (coherent anti-Stokes Raman Spectroscopy)-detectable label, a multiphoton fluorescence microscopy-detectable label, a harmonic microscopy-detectable label, an acoustic imaging-detectable label, an impedance spectroscopy-detectable label or a reflectance spectroscopy-detectable label. The methods and systems can further comprise detecting at least one location of the plurality of magnetizable objects within the patient, and can further comprise a feedback controller to control at least one externally applied magnetic field in response to said detection.

Additionally provided are devices for externally applying a shaped magnetic field to a patient sufficient to direct a plurality of magnetizable objects, or a ferrofluid composed thereof, to a first desired target volume within the patient, wherein said device comprises an array of independently operable magnets, where the magnets may be permanent magnets, electromagnets, or a combination thereof, and a Magnetic Field generator capable of dynamically and individually controlling and shaping the direction and strength of the magnetic fields of said magnets to thereby direct the plurality of magnetizable objects to the first desired target volume within the patient. Also provided are devices for externally applying a shaped magnetic field to a patient sufficient to move a plurality of magnetizable objects, or a ferrofluid composed thereof, from a first desired target volume within the patient to at least one second desired target volume within the patient, wherein said device comprises an array of independently operable magnets, where the magnets may be permanent magnets, electromagnets, or a combination thereof, and a Magnetic Field generator capable of dynamically and individually controlling and shaping the direction and strength of the magnetic fields of said magnets to thereby move the plurality of magnetizable objects from, the first desired target volume to the at least second desired target volume.

The devices can further comprise a sensor system capable of detecting at least one location of the plurality of magnetizable objects within the patient. The magnets can be independently operable electromagnets, or can be independently adjustable permanent magnets. The magnets can comprise a combination of independently operable electromagnets and independently adjustable permanent magnets. The magnetizable objects can comprise a detectable label, which is a radioisotopic label, a paramagnetic label, a CARS (coherent anti-Stokes Raman Spectroscopy)-detectable label, a multiphoton fluorescence microscopy-detectable label, a harmonic microscopy-detectable label, an acoustic imaging-detectable label, an impedance spectroscopy-detectable label or a reflectance spectroscopy-detectable label. The device can further comprise detecting at least one location of the plurality of magnetizable objects within the patient, and can further comprise a feedback controller to control at least one externally applied magnetic field in response to said detection.

Additional advantages and features of the present invention will be apparent from the following detailed description, drawings and examples, which illustrate preferred embodiments of the invention.

For example, the notation 3/18 in the brain indicates that 3 out of 18 patients exhibited metastases in the brain.

Figure 12:
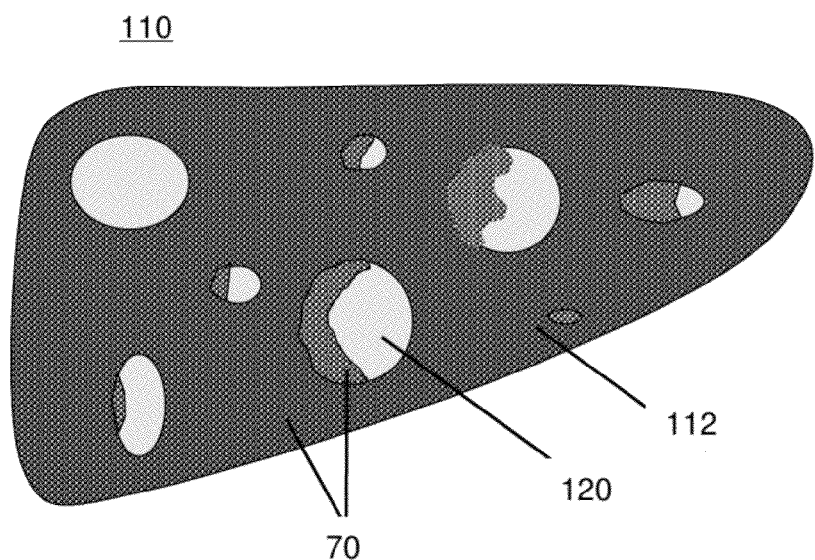

FIG. 12 depicts a schematic view of magnetizable objects in a target volume (the liver) according to a method of an embodiment of the present invention.

Figure 13:
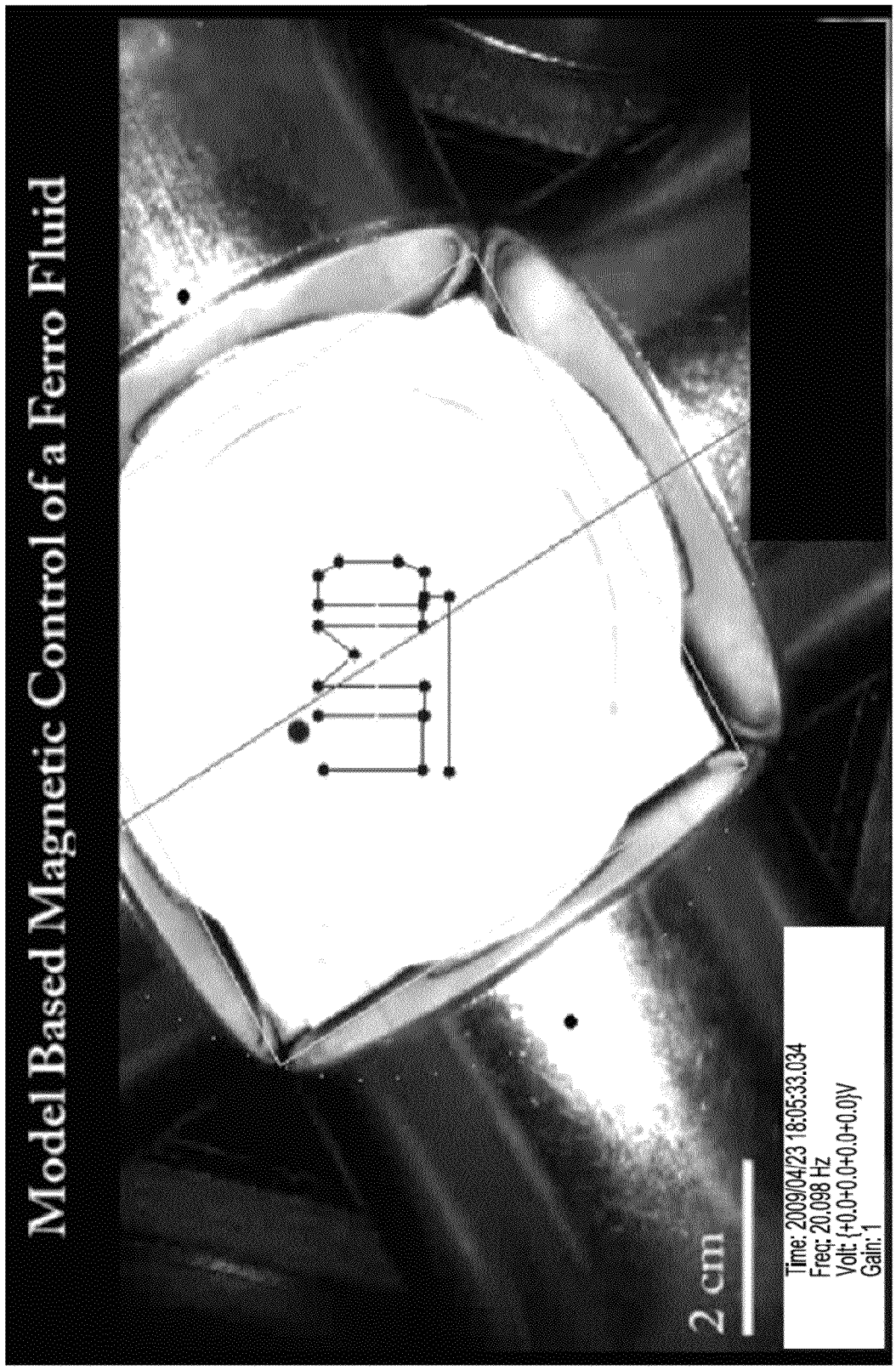

FIG. 13 depicts the control of a single drop of ferrofluid, according to an embodiment of the present invention.

DETAILED DESCRIPTION OF THE INVENTION

Reference will now be made in detail to the presently preferred embodiments of the invention, which, together with the drawings and the following examples, serve to explain the principles of the invention. These embodiments are described in sufficient detail to enable those skilled in the art to practice the invention, and it is to be understood that other embodiments may be utilized, and that structural, electrical, magnetic, biological, chemical, medical, and control algorithm changes may be made without departing from the spirit and scope of the present invention. Unless otherwise defined, all technical and scientific terms used herein have the same meaning as commonly understood by one of ordinary skill in the art to which this invention belongs. Although any methods and materials similar or equivalent to those described herein can be used in the practice or testing of the present invention, the preferred methods, devices, and materials are now described.

In conventional magnetic drug therapy, an external magnet is held outside the body to focus magnetic or magnetizable particles. In magnetic drug delivery magnetizable particles or other objects are attracted solely to regions of highest magnetic field strength, as illustrated by the following equations. Further, conventional magnetic drug delivery relies on static magnetic fields. The force density (units N/m$^3$) on a fluid element of a ferrofluid (a collection of magnetizable particles or objects) is determined by Equation (1), where a is the radius of the $$\vec{f}_{mag} = \frac{2\pi a^3}{3}\mu_0 C \frac{x}{1+X/3}\nabla(\vec{H}^2)[\text{unsaturated}, \mu_0|\vec{H}| < 0.1T] \quad (1)$$

$$= C\frac{4\pi a^3}{3}\mu_0 \vec{M}_{sat} \cdot \nabla \vec{H}[\text{saturated}, \mu_0|\vec{H}| \geq 0.1T]$$

particles, $\mu_0 = 4\pi \times 10^{-7}$ V s/A, m is the permittivity of vacuum, C is the local concentration of particles (number per m$^3$), $\chi$ is the magnetic susceptibility (a material property, nondimensional), and H in SI units A/m is the externally applied magnetic field strength. The first equation holds when the applied field is low (<0.1 Tesla). For higher fields, the magnetization saturates to $M_{sat}$~90 A m$^2$/kg at body temperature (because M lines up with H, by the chain rule $\nabla H^2$ and $M_{sat}\nabla H$ will point in the same directions). The magnetic forces go as the gradient of the applied magnetic field squared. Thus forces are from regions of applied low to high magnetic field strength: the magnetic particles are attracted by any single magnet. The force-per-particle is very small: a single 250 nm diameter magnetite core particle under a 0.5 Tesla magnetic field varying over a length-scale of ~1 cm will experience a force of just ~$10^{-13}$ Newtons. The above equations apply for spherical paramagnetic or ferromagnetic particles but like equations apply more generally to magnetizable objects of any shape or size; these objects will still be attracted to regions of highest magnetic field strength.

In current magnetic drug delivery, because the highest magnetic fields occur at the corners of a magnet, the particles will get as close to the magnet as they can without leaving the body and thus concentrate at the skin surface. As a result, even with the highest 1-8 Tesla magnetic fields considered safe for human application, the particles cannot be focused to tumor targets deeper than about 5 centimeters into the body by conventional means. Thus, deep tissue targets such as tumors in the lungs, intestines, or liver cannot be treated using conventional magnetic therapy. This problem is a direct consequence of Earnshaw's Theorem, which states that static magnetic forces cannot produce a stable equilibrium of magnetizable objects at a distance. This also means that magnetizable objects cannot be confined to a desired target volume that includes deep regions.

This inability of conventional treatment methods to treat deep targets or whole desired volumes also causes difficulty in treating metastatic cancer, which can be wide-spread throughout one or more anatomic zones of the body. There is also difficulty in treating poorly vascularized tumors, because the incomplete vasculature results in poor delivery of therapeutic agents to these lesions, and conventional magnetic drug therapy is both unable to achieve a high enough local concentration of therapeutic agents to achieve diffusion into the tumor or a mechanism to drive the agents into the tumor tissue (current magnetic drug delivery does not sweep magnetizable objects from one volume into another).

A. Systems and Methods for Magnetic Control

The problems in conventional magnetic therapy have been solved by developing methods and systems for containing or moving magnetizable objects at a distance, to volumes, and through volumes using shaped magnetic fields. Here shaped means that the magnetic field is precisely chosen to achieve a task, e.g. to target a whole desired volume or to sweep from one volume to another. This shaping can be done in space and in time and can be mathematically sophisticated (the result of solving optimization tasks that enable said shaping). Embodiments of the present invention rely on using a magnetic field created by sets of opposing magnets to sweep and to bypass Earnshaw's Theorem to enable deep focusing to whole volumes.

When magnetizable objects are injected into a patient's blood, they circulate throughout the body via the circulatory system and are directed by shaped magnetic fields to the whole of a desired target volume, where such directing can be achieved over time. FIG. 8 is a representative example showing precisely chosen actuation of 8 magnets over time to direct magnetizable objects to the whole of a centered deep region (positive targeting). This sequence is more than just targeting successive parts of the whole volume in sequence because no static combination of magnets can access the deep center region, instead it exploits the dynamics of the ferrofluid and shapes the magnetic fields to move the ferrofluid primarily through the center. Thus this sequence is highly not obvious to one skilled in the art. See, e.g., B. Shapiro, "Towards Dynamic Control of Magnetic Fields to Focus Magnetic Carriers to Targets Deep Inside the Body", Journal of Magnetism and Magnetic Materials, 321(10):1594-1599 (11 May 2009), which is incorporated by reference herein in its entirety.

Other embodiments use a magnetic field to prevent the magnetizable objects from concentrating at undesirable locations in the body, thus forcing the objects to be contained in the desired target volume because they cannot go elsewhere (negative targeting). This can be done, for example, by opposing two magnets with opposite polarity to create a zero magnetic field between them. Forces on the magnetizable objects will go from low to high magnetic field strength. Since the magnetic field between the two magnets is now zero, or approximately zero, all forces on the magnetizable objects will directed out from this region. Thus the magnetizable objects will be ejected out of the region between the two opposite polarity magnets (see FIG. 5B).

In yet other embodiments (sweeping), a magnetic field is used to move the magnetizable objects along one or more directions inside the body, such that the objects pass through a target volume, for example from side-to-side and upwards and downwards. For example, if magnetizable objects have been delivered to a liver by blood flow or magnetic means, and that liver contains metastases that are poorly vascularized, then applying a single magnet on the right will sweep the ferrofluid (the collection of magnetizable objects) from the left side of each metastases that does not yet contain ferrofluid to the right, thus sweeping through each metastases, regardless of its size, shape, or location in the liver (as shown in FIG. 12). The process can then be repeated to sweep from right to left: ferrofluid can be allowed to accumulate in the liver again, and then a magnet can be applied on the left. The sequence can repeat (then top sweep, then bottom sweep) to best ensure that all parts of all metastases have been swept by the ferrofluid, thus providing treatment to all metastases in the liver. This movement is particular desirable in that it causes the objects to move from vascular tissue into adjacent incompletely-vascularized tissue where the objects otherwise could not penetrate. It is clear that like methods can be used for other regions, organs, sweep directions, sequence of directions, and other modifications that are in the spirit described above.

Therefore, magnetizable compositions (e.g., chemotherapeutic agents attached to magnetizable particles) can be contained in a target volume (and/or moved within the target volume) containing tumors or other diseased tissue deep in a patient's body by an externally applied magnetic field, ensuring high concentrations at many tumor locations, e.g. the majority of the clinically significant tumors in various types of cancer, and lower concentrations elsewhere in the patient's body. The advantages of the magnetic focusing system and methods include: being able to effectively treat the majority of clinically relevant metastatic tumors since these are often confined to a specific anatomical region (e.g. the upper torso in breast cancer) while decreasing dosage and hence life-threatening side-effects in the rest of the body; being able to treat the majority of tumors at once even if their size, location, and properties are not known and cannot be determined; being able to treat very many tumors at once instead of attempting a one-by-one tumor treatment which is typically not feasible for advanced disease; being able to access hard-to-reach metastatic tumors by sweeping therapy in from surrounding, nearby, or in contact easier-to-access regions; the ability to use more highly-toxic therapeutic agents than could be used with conventional delivery methods due to the ability to better focus them to tumors and to thus use lower concentrations systemically; enhanced efficacy of therapeutic agents with short half lives, because the agents can be concentrated to their targets quickly; and reduced expense, because smaller amounts of therapeutic agents are required.

As noted above, the task of controlling many magnetizable objects capable of independent movement, or a magnetizable ferro-fluid, to a target is more difficult than controlling a single object to a target. It is understood to a person skilled in the art that while attempting to control one object, all other objects may be driven away from the target. A control method is needed that controls all, or a majority of the, magnetizable objects at once (that controls very many object at once, a fluid). Currently, there is no prior-art that enables such simultaneous control of many magnetizable objects to whole desired target volumes or to many hard-to-access metastatic regions at once.

Figure 1:
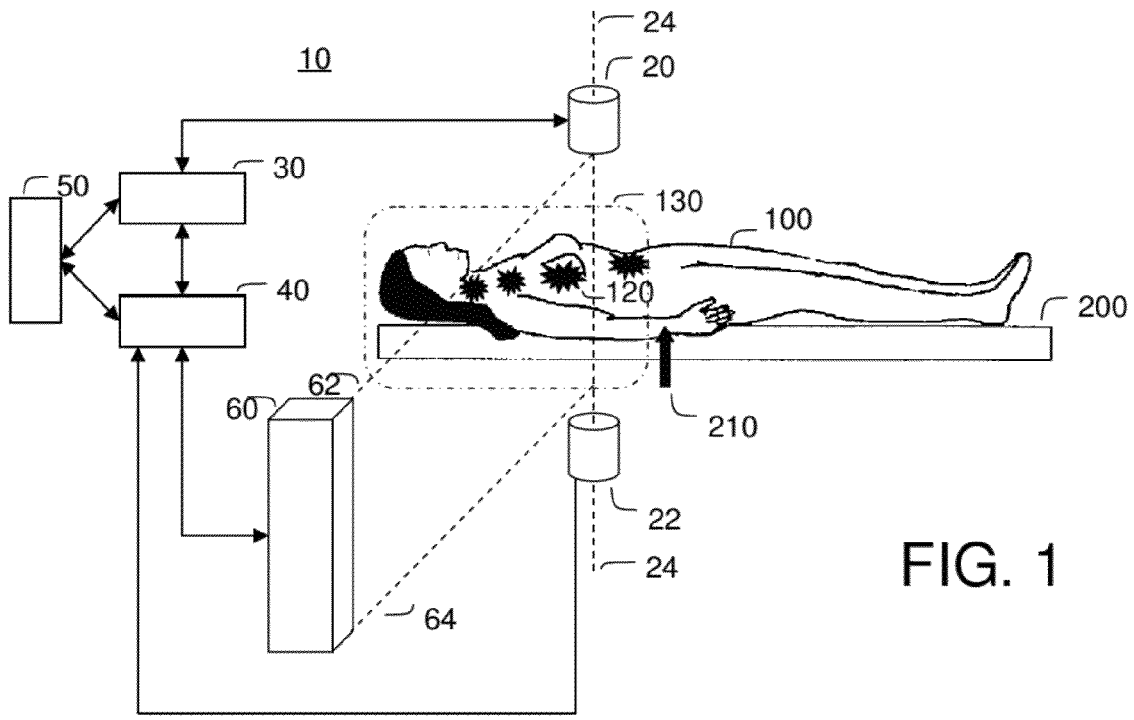
FIG. 1 is a schematic view of a magnetic containment system according to an embodiment of the present invention.

Referring now to FIG. 1, an exemplary embodiment of the magnetic containment system is shown. The therapeutic methods may be performed on a patient 100 following a determination of the presence of a diseased material 120 (e.g., a tumor, infection, abcess, stenotic lesion, etc.) in the patient. A target volume 130 for treatment is determined based on the type and location of the diseased material. For example, if the diseased material is a tumor, the target volume is designed to include the tumor volume, plus margins of spread to account for undetected growth around the tumor, plus margins of safety. Similarly, if the diseased material is a metastasized tumor, or many metastasized tumors, the volume is designed to include the regions of most probable clinically important metastasis; for example for breast cancer, the upper torso and head may be included in the target volume because breast cancers most commonly metastasize to the lungs, liver and slightly less often the brain; and for prostate cancer, the posterior torso and hips may be included in the target volume because prostate cancers most commonly metastasize to the spine and hips. Some advantages of selecting a target volume in this manner include not needing to actually detect or know the precise location of each tumor within the patient, whether prior to or during treatment, and the ability to treat multiple tumors simultaneously. An expert in cancer treatment can choose such a volume wisely based on his or her knowledge of disease progression to include the majority of clinically relevant tumors that, if left untreated, will cause morbidity and mortality. This chosen volume may include thousands of tumors.

The system 10 is designed with opposing magnets 20, 22 (here only 2 are shown, more are possible) arranged around a patient 100. The gap between magnets 20, 22 therefore must be large enough to permit a patient's body or body part to be inserted between the magnets. The patient may be arranged on bed 200 as necessary to achieve effective positioning of the system 10 relative to the target volume 130 to be treated. Although not shown here, in certain embodiments the magnets may be positioned or controlled in order to achieve negative containment, i.e., they may be positioned and actuated in such a manner as to eject the magnetizable objects from portions outside the volume thus restricting the objects to remain primarily within the target volume (negative targeting).

Magnetizable objects may be administered to the patient by any suitable means, exemplified here by intravenous injection 210 into the blood vessels of the arm. Depending on the type and location of the diseased tissue, suitable administration methods may include, but are not limited to, ocular, intranasal, inhalation, oral, buccal, sublingual, mucosal, rectal, topical, transdermal, subcutaneous, intra-arterial, intravenous, intramuscular, intraperitoneal, parenteral, or infusion methodologies. Administration can be localized, for example by injecting the magnetizable objects into, or near, the tumor location, or systemic, for example intravenous injection.

In FIG. 1, magnets 20, 22 are connected to a Magnetic Field (MF) generator 30, which may be a dynamic or static magnetic field generator, and also to a feedback controller 40, both of which are connected to a control computer 50. The MF generator 30 produces current to magnets 20, 22, and can vary the current as directed by feedback controller 40 and/or control computer 50. Thus, the strength of magnets 20, 22 can be varied to create a dynamic magnetic field around the area to be treated in the patient. The magnetic field can be varied in both space and time in order to focus the magnetizable objects to (and/or through) the target volume 130 in the patient's body.

The location and concentration of the magnetizable objects within the patient's body 100 can be monitored by a sensor system 60, which may operate by any suitable means, such as magnetic resonance, radiation sensing (e.g., sensing of x-rays, gamma rays, etc.), ultrasound, or the like. A non-limiting example of a magnetic resonance sensor system is shown here, which creates an image plane shown here bounded by lines 62, 64, and magnetic axis 24, thereby collecting data regarding the position of the magnetizable objects in the patient's body. Feedback controller 40 uses the data collected by the sensor system 60, for example to direct the MF generator 30 to vary the magnetic field in order to guide the movement of the magnetizable objects as desired, for example toward or within the target volume 130. An operator or technician may control or monitor the desired behavior via a control computer 50.

The sensor system may additionally or alternatively be capable of detecting a detectable label that may be a component of, or associated with, the magnetizable objects or the ferrofluid containing such objects. The detectable label may be, for example, a radioisotopic label (e.g., $^{213}$Bi, $^{11}$C, $^{14}$C, etc.), a paramagnetic label (which may be chelated to a chemical ligand such as diethylene triamine pentaacetic acid (DTPA), 1,4,7,10-tetraacetic acid (DOTA), 10-(2-hydroxypropyl) 1,4,7-triacetic acid (HPDO3A), or 4,7-triacetic acid (DO3A), a CARS (coherent anti-Stokes Raman Spectroscopy)-detectable label, a multiphoton fluorescence microscopy-detectable label, a harmonic microscopy-detectable label (especially a second and third harmonic microscopy detectable label), an acoustic imaging-detectable label, an impedance spectroscopy-detectable label, or a reflectance spectroscopy-detectable label.

In a preferred embodiment, sensor system 60 is a gamma camera or PET scanner able to detect the in vivo position of the magnetizable objects via their emission of gamma rays. Suitable gamma cameras are commercially available, for example from Nuclear Imaging Services and Nuclear Cardiology Systems. As of 2005, CCD gamma cameras were capable of achieving 0.1 mm resolution at 10 frames per second, and are expected to improve resolution and speed in the future. Currently, gamma cameras are better able to approach real-time sensing than magnetic resonance imaging, which is comparatively slow. However, the type of sensor system chosen may depend not only on the speed of feedback desired, but the magnetizable object composition as well. Objects for use with a gamma camera must be radioactive and emit gamma rays, which could be disadvantageous for certain patients. Likewise, x-rays, ultrasound, or other sensing means may be used to provide positional feedback.

Figure 2:
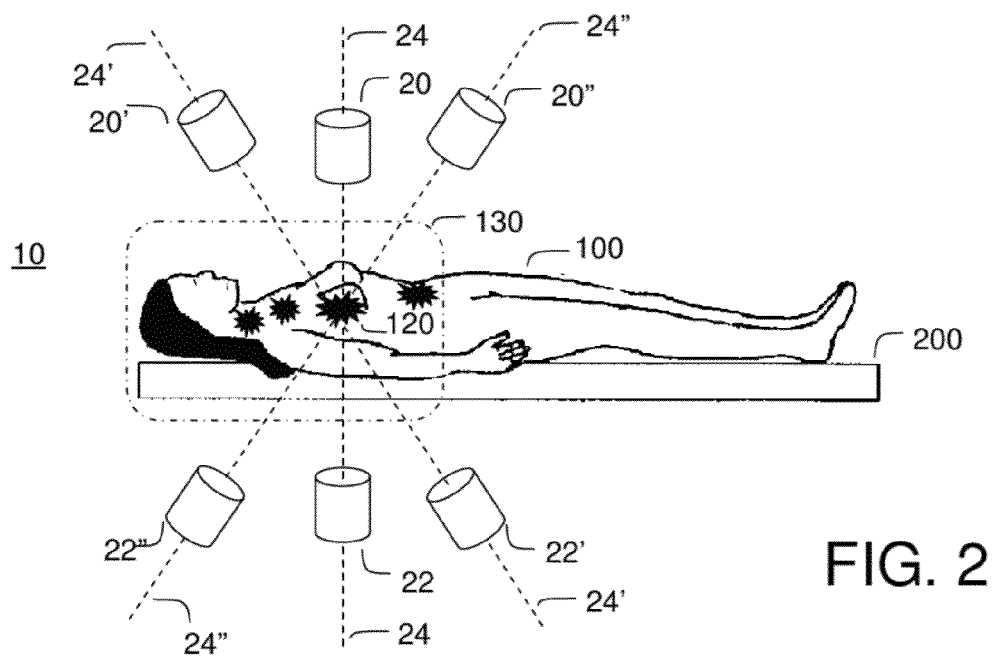
FIG. 2 is a schematic view of magnet orientation in a magnetic containment system according to an embodiment of the present invention.

Although FIG. 1 depicts only a single set of magnets, and a single sensing plane, it is understood that the systems of the preferred embodiments may use multiple sets of opposing magnets. In a non-limiting example, six to ten magnets in total are used. The magnets are arranged in opposing sets, for example as depicted in FIG. 2, which shows six magnets 20, 20', 20", 22, 22', 22" arranged about the patient 100 so as to maximize three-dimensional containment of the magnetizable objects. For ease of illustration, FIG. 2 does not depict any of the components of system 10 other than the magnets.

Figure 11:
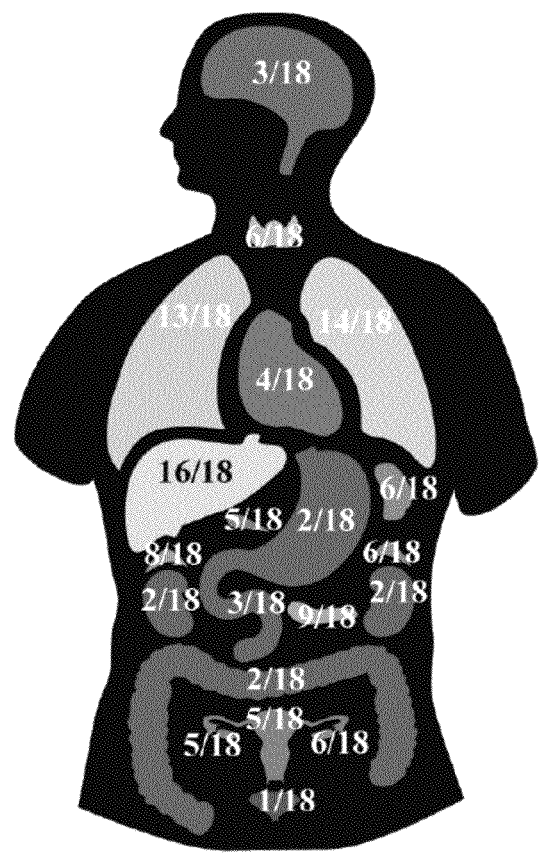
FIG. 11 depicts the frequency of various metastases observed in a sample of metastatic breast cancer autopsies overlain on a schematic of major organs in the human body.

Many patients present to the clinic with widely metastatic cancer, consisting of hundreds to thousands of tumors that vary in size from grossly visible lesions to small microscopic foci. As a practical matter, not all of the tumors can be treated surgically or even by focused radiation therapy. Thus, one approach to the management of patients with this dire diagnosis is to focus on treating the subset of tumors that are the most clinically important, the ones that cause symptoms (morbidity) and death (mortality) if left untreated. In many cancers (for example, breast cancer, prostate cancer) the clinically significant tumor burden is typically present in specific regions of the body. Thus, for example, the target volume for breast cancer is the upper torso and head, because the primary areas of metastasis are the lungs, liver and brain, and the target volume for prostate cancer is the posterior torso and hips, because the primary areas of metastasis are the spine and hips. This is depicted in FIG. 11 for breast cancer.

The ability to focus chemotherapy to the anatomical region that contains the significant tumor is clinically important—it will treat the main burden that causes morbidity and mortality but it will spare the rest of the body (bone marrow, immune system, skin and gut cells, and brain cells in the rest of the patient). An ability to confine chemotherapy to an anatomical region through magnetic drug targeting will effectively treat all metastatic foci in that region (without needing to know the precise anatomical locations of the tumors), and is more practical than attempting to perform discrete focusing to each specific tumor, which could number in the thousands, many of which are microscopic and not visible on conventional imaging scans.

It has been discovered by the inventors and their colleagues via autopsies performed on patients with metastasized cancer, that many metastatic tumors are poorly vascularized and have little blood flow to them. This means these metastases are largely isolated from drugs injected systemically into the blood stream and has thus motivated the need for development of the sweep methods and systems proposed in this application. This is depicted in FIG. 12, which shows poorly vascularized metastases 120 in a patient liver 100. Using the methods of the present embodiments, magnetizable nanoparticles are introduced into the bloodstream of the patient, and pass through normal vascular circulation into the target volume surrounding the metastatic tumors. In one embodiment, magnetic fields are then applied to sweep the particles a short distance into and through the metastatic tumors within that volume. This sweeping movement ensures that the particles are moved through the target volume and pass through all, or the majority of, the metastatic tumors. In between the movements, the magnetic field may be turned off so that the particles can re-accumulate around the tumors, or, in another embodiment, regional magnetic targeting may be used to again direct them to the first volume that surrounds, is near, or is otherwise in contact with the metastases. The sweeping field is then applied again to move the particles in another direction and this process can repeat in multiple directions to access the metastases from all sides and thus better ensure that every part of each metastases has received treatment.

In this embodiment shaping of the magnetic field in time, space, or both, is used to both direct ferrofluid to the first volume (regional targeting) and then to sweep it into the second volume containing the poorly vascularized metastases (sweeping). In another embodiment the magnetic field is used to direct magnetizable objects to a first volume or volumes that are near, surround, or are otherwise in contact with the metastases in the second volume, and then non-magnetic means move the ferrofluid from the first volume to the second. In this embodiment magnetic control is used for the first step only. In a third embodiment, the ferrofluid accumulates in the first volume by non-magnetic means (e.g. by the usual blood flow, by diffusion, or by sequestering in the liver) and then the magnetic field is used to sweep ferrofluid from the first volume to the many metastases. Exact knowledge of the location, size, and properties of the metastases is not required for these sweep method to be effective. The sweep method has the advantage that it treats all, or the majority of the metastases simultaneously, thus not requiring an impractical and unfeasible one-by-one treatment of thousands of metastatic tumors.

Figure 3:
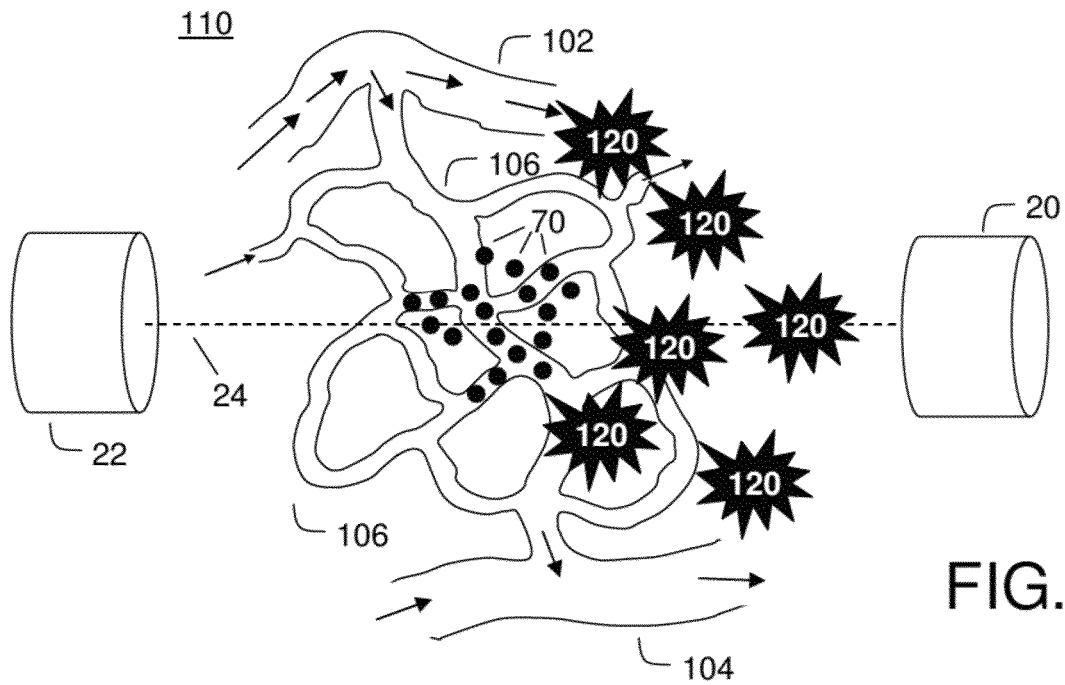
FIG. 3 is a schematic view of a magnetic containment treatment according to an embodiment of the present invention.

FIG. 3 depicts a magnetic containment treatment at a very narrow focus. A cut-away view of the patient's liver 110 and blood vessels including arteriole 102, venule 104, and capillaries 106 in the patient is shown, with arrows indicating the direction of blood flow. Magnetizable objects 70 are also shown in the capillaries 106 and the surrounding tissue near diseased material 120. For ease of illustration, only magnets 20, 22 and their magnetic axis 24 are shown here. When first injected, the magnetizable objects 70 will be trapped by the magnetic forces at the regions of highest magnetic field, which occur along magnetic axis 24. However, the objects 70 may not be correctly positioned on magnetic axis 24 to achieve optimal treatment of diseased material 120. For example, FIG. 3 depicts the magnetizable objects 70 as clustered to the left of diseased material 120. It is now possible to turn on the right magnet to move the cluster of magnetizable objects to the target tumor. This is a specific example of dynamically turning magnets on and off to direct magnetizable objects to deep targets by feedback control.

Figure 4:
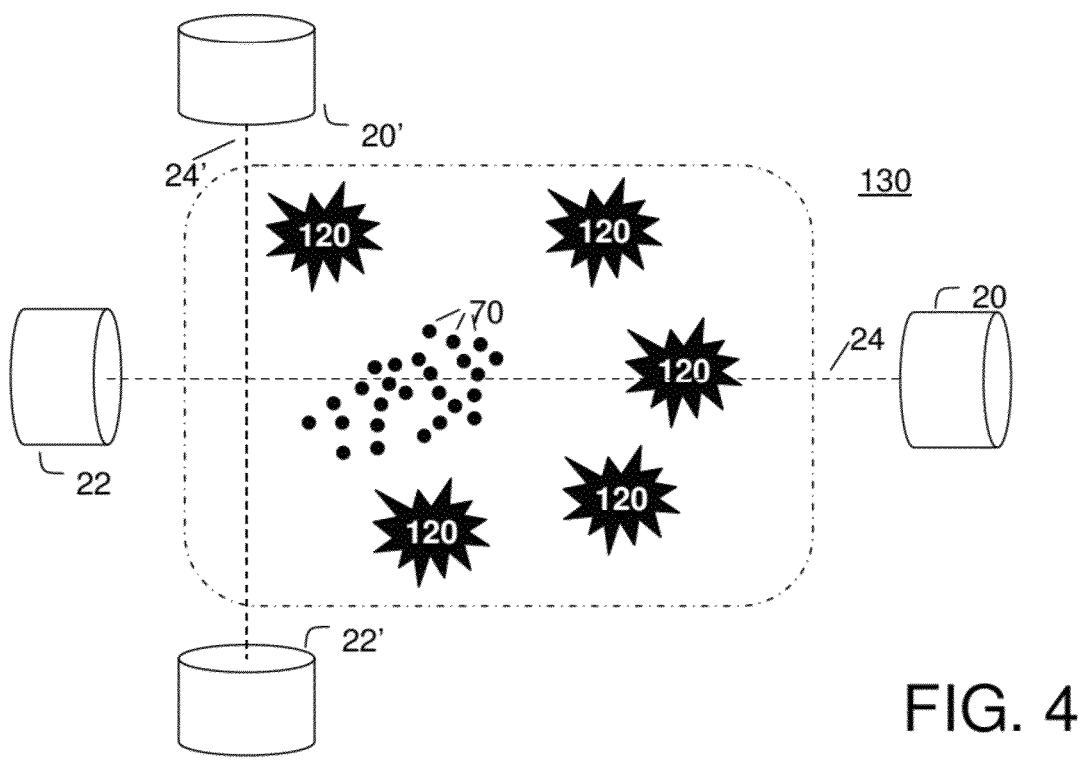
FIG. 4 is a schematic view of a magnetic containment treatment according to an embodiment of the present invention.

FIG. 4 depicts a magnetic containment treatment at a broader focus. In this embodiment, multiple tumors 120 are found in the patient's body, and the target volume 130 is designed to encompass them all. Magnetizable objects 70 have been transported to the target volume 130, and are now being contained by the magnetic fields generated by magnets 20, 20', 22, 22'. This containment can be achieved by solving an optimization problem similar to the one in FIG. 8 to always move the majority of magnetizable objects more into the desired volume. As shown here schematically, the magnetizable objects 70 cluster along the magnetic field occurring along horizontal magnetic axis 24, but are repelled by the magnetic field occurring along vertical magnetic axis 24' where two magnets oppose each other, so that the particles are directed into the target volume 130.

Any person knowledgeable in the art will understand that there are very many options to optimize and shape magnetic fields, in space and time, to direct particles to volumes (positive targeting) or keep them out of undesired volumes (negative targeting), and that, once the examples provides in FIGS. 3, 4 and 8 have been understood, many other examples are possible. Moreover, since the fields can be complex the most efficacious way of picking necessary fields is by optimization methods, such as described in equations (9) to (13) and associated text or by related methods, and not by enumerating possible magnet orientations.

Information regarding the position of the magnetizable objects can be obtained by sensor system 60 and collected by feedback controller 40, which then directs the MF generator 30 to change and shape the magnetic field to best move the objects. For example, in the situation depicted in FIG. 3, the position of the magnetizable objects 70 would be corrected by increasing the strength of the right magnet 20 relative to the strength of the left magnet 22, thereby focusing the magnetizable objects 70 to the right and into diseased material 120. The alteration of the magnet strength and the varying of the magnetic field is carried out in accordance with the positional feedback received from the sensor system in real-time or as close to it as possible, such that if the magnetizable objects begin to drift away from the target volume, the appropriate set (or sets) of magnets are controlled to correct the object positions. This control is highly complex due to the need to focus a large number of independent magnetizable objects at the same time and again is the result of sophisticated mathematical optimizations to determine an appropriate set of magnet actuations or reorientations.

Figure 5A:
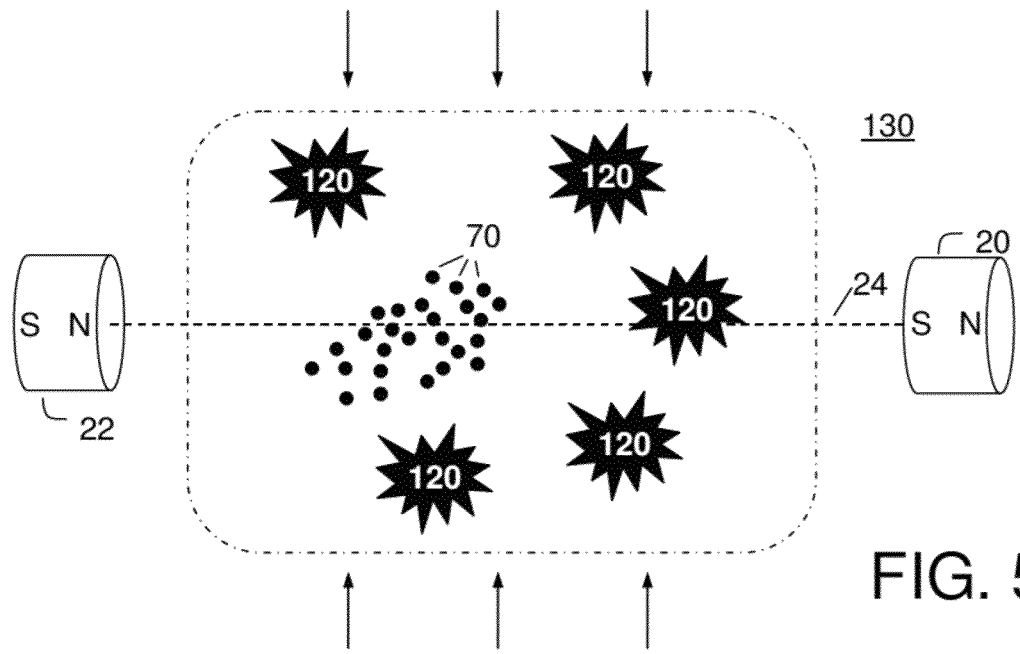
FIG. 5 depicts schematic views of magnetizable objects in a target volume according to a method of an embodiment of the present invention. Panel A depicts magnetic force pointing in towards a magnetic field strength maximum inside the target volume (positive targeting), and panel B depicts magnetic force pointing out from a magnetic field strength minimum inside the target volume (negative targeting).
Figure 5B:
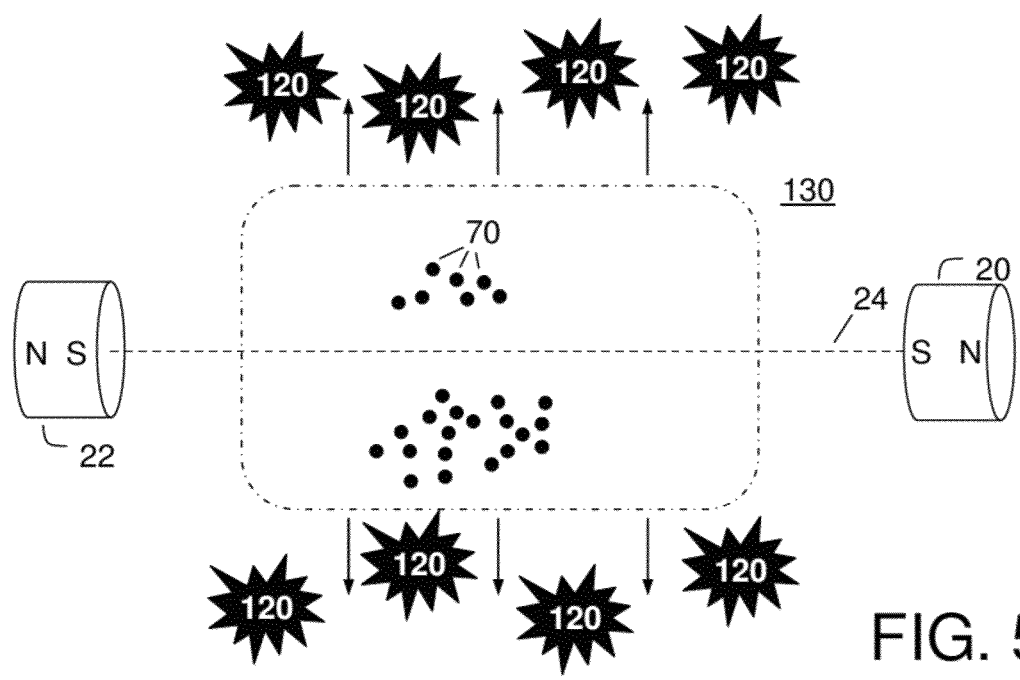

FIG. 5 depicts magnetic forces acting on the magnetizable objects 70 within the target volume 130, which also contains diseased tissue 120. In FIG. 5A, the magnetic field strength is at a maximum inside the target volume, thereby exerting a force (shown by arrows) on the magnetizable objects that points into the volume. In FIG. 5B, the magnetic field strength is at a minimum (since now magnets 20 and 22 oppose each other, are oriented in opposing directions, and this creates a magnetic field cancellation between them) thereby exerting a force (shown by arrows) on the magnetizable objects that points out of the volume. Further, motion of the magnetizable objects may be directed in curved paths, or in paths made more readily available by the body (e.g. through paths provided by vasculature, the lymphatic system, interstitial fluid, or air gaps).

Figure 7:
FIG. 7 depicts a vasculature model of the human body.
Figure 8B:
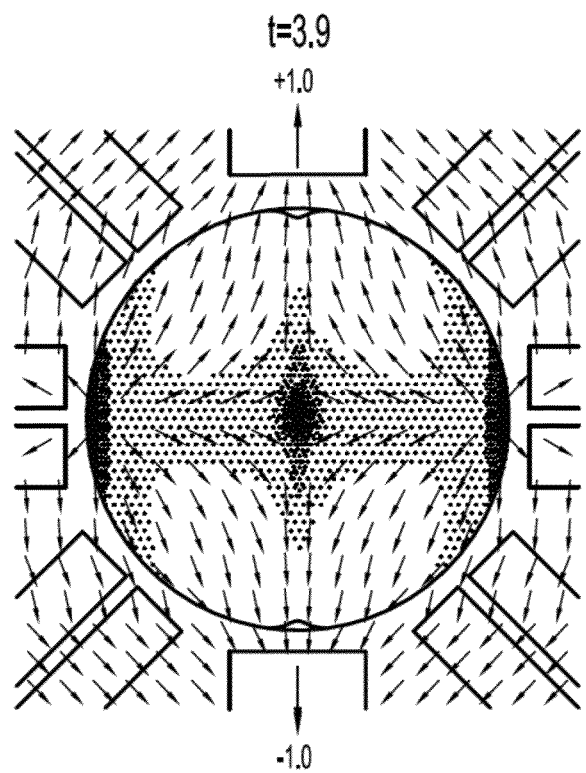
FIG. 8 (Panels A-C): Panel A shows constant actuation: ferrofluid transport due to turning on the 5th (far left) magnet. Sub-Panel i) The magnetic energy surface $U=-kH^2$ is plotted along the z axis to show ferrofluid flowing downhill along the force directions $F=-\nabla U$ with the resulting averaged concentration shown by the grayscale coloring here and in Sub-Panel ii). Panel B shows dynamic control: magnets are now turned on and off to transport ferrofluid to the center. The first 5 Sub-Panels (i-v) show ferrofluid concentration and magnetic actuation with the corresponding magnetic energy surfaces. Energy surfaces for the last 4 panels are 90 degree flips of the ones shown. Grayscale coloring denotes concentration (scale bar same as in Panel C). On magnets are illustrated by heavy black lines with weighted thick gray arrows and numbering showing magnet strength and orientation (South to North outwards is a positive polarity). Thin gray arrows (normalized to unit length) show magnetic force directions which match the gradients of the magnetic energy surfaces (forces point down the surfaces). Panel C shows the resulting time-averaged ferrofluid concentration. Note the on-average hot spot at the center target.
Figure 8B:
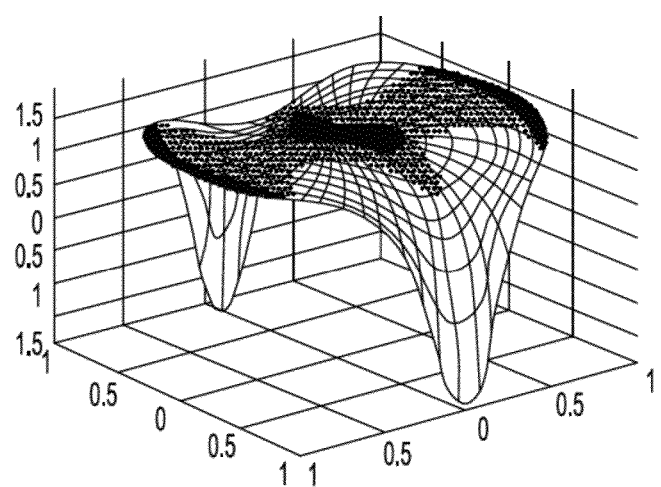
Figure 8B:
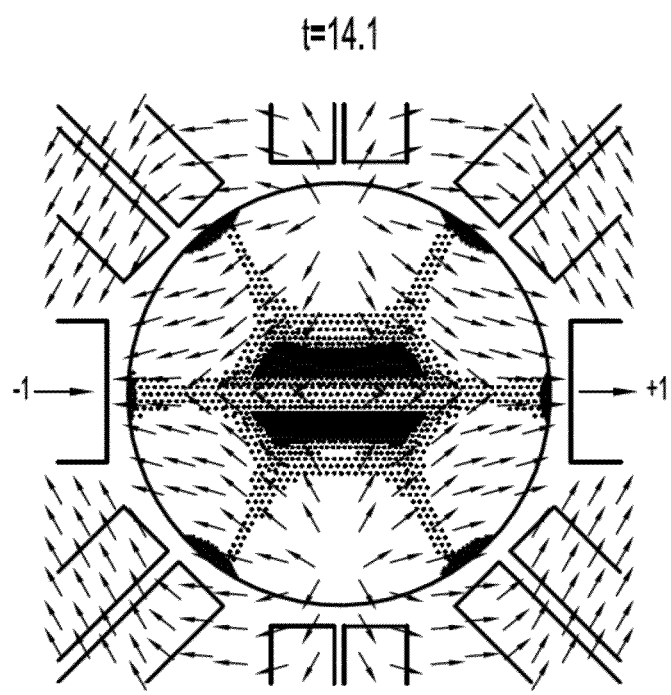
Figure 8B:
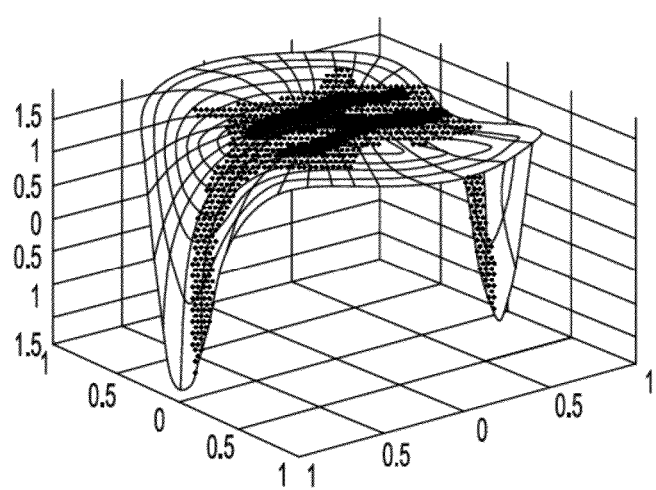
Figure 8C:
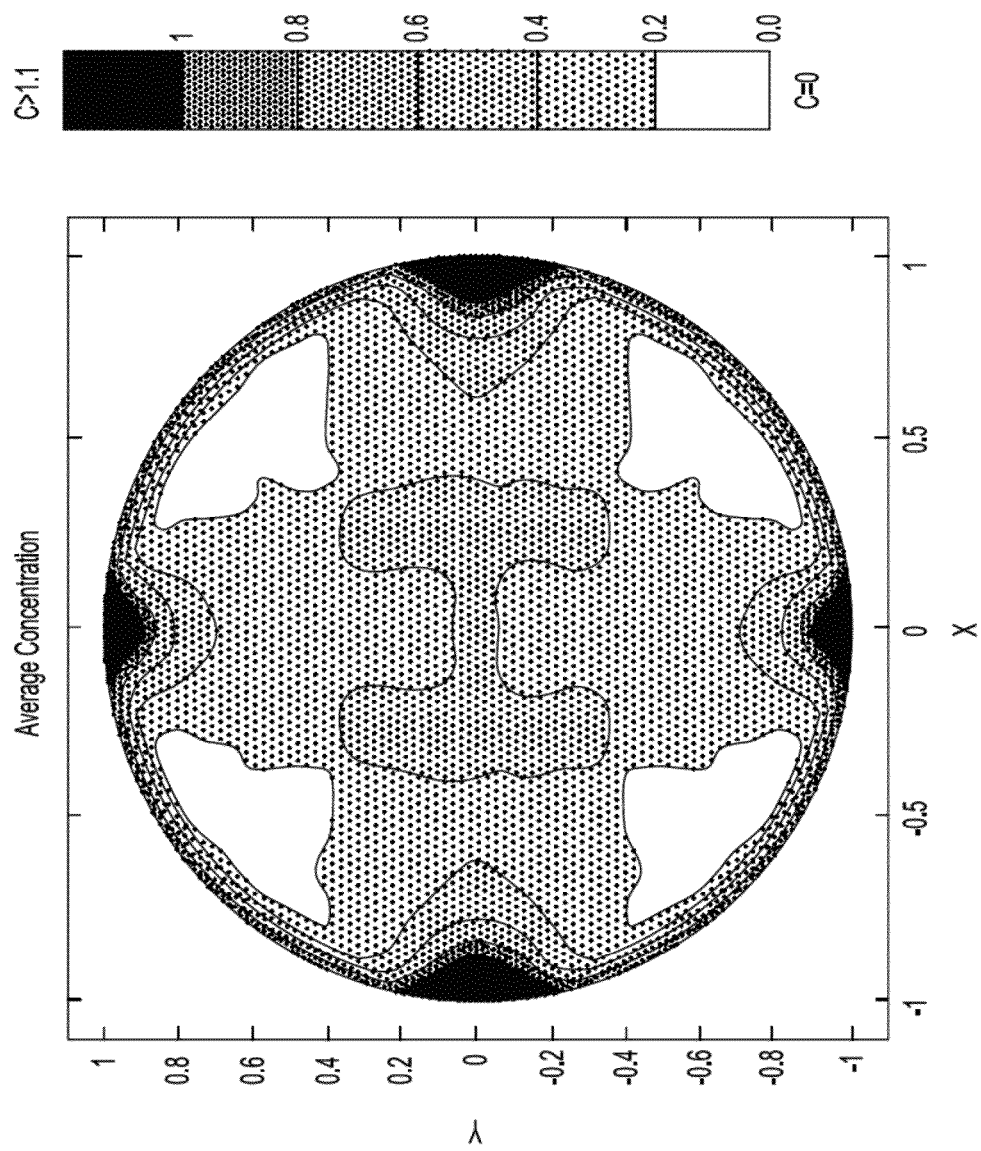

Another example of shaping magnetic fields to direct particles to a target volume is shown in FIG. 8. Details for the control are noted in the figure caption and in B. Shapiro, "Towards Dynamic Control of Magnetic Fields to Focus Magnetic Carriers to Targets Deep Inside the Body", Journal of Magnetism and Magnetic Materials, 321(10):1594-1599 (11 May 2009), which is incorporated by reference herein in its entirety. The desired target volume is the center. Here magnetizable objects are first concentrated to the North/South edges of the body (represented by the circular domain). The magnetic field is then shaped in space to cause the objects to move to the center with a minimum of spillage off to the sides. This is achieved by solving a quadratic optimization problem. Once spillage off to the sides can no longer be avoided the magnetizable objects, the ferrofluid, are concentrated to the East/West edges of the body. Now they are brought to the center again by a second optimization, again with minimum spillage. The process repeats to accumulate the ferrofluid to the desired center target. It should be understood that this scheme can be modified to work in 3-dimensions, in a body of a different shape, in the presence of vasculature or other transport networks, as shown in FIG. 7, to access a volume at a different deep location (e.g. off center but still deep), or to access a volume of a different shape.

It should be understood that when containment or movement of the magnetizable objects is discussed, the containment or movement need not be of every object, but only a majority thereof. For example, in a preferred embodiment, at least 50, 55, 60, 65, 70, 75, 80, 85, 90, or 95 percent of the magnetizable objects are contained in, or moved through, the desired target volume. In a particularly preferred embodiment, at least 60, 70, 80, or 90 percent of the magnetizable objects are contained in, or moved through, the desired target volume, and in a more preferred embodiment, at least 75 percent of the magnetizable objects are contained in, or moved through, the desired target volume.

Figure 6A:
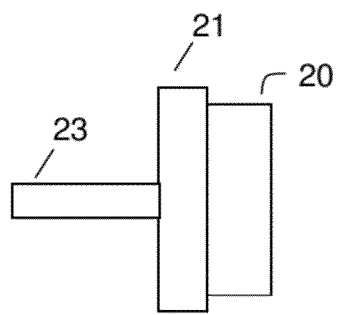
FIGS. 6A and 6B are schematic views of magnets according to an embodiment of the present invention.
Figure 6B:
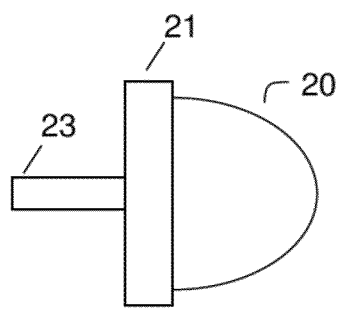

The pairs of magnets are spaced apart from each other such that the patient or the body part to be treated is be inserted between the magnets. For example, although FIGS. 1 and 2 depict the entire patient body in between the magnets, for certain applications it is contemplated that only a part of the patient, for example the patient's leg, might be inserted between the magnets. For example, a focusing distance of 30 cm from each magnet is desirable because it enables a gap of 60 cm between magnets (more than half a meter), which should be sufficient to target deep tumors even in obese patients. To find how forces on the magnetizable objects scale with focusing distance, magnet dimensions and strength, Biot-Savart's law was integrated over a planar coil arrangement (as in the experiment of Example 1, coil radius a=3 cm, length L=1 cm) to find the following solution for the magnetic field along the vertical magnet axis in Equation (2), where z is the distance from the magnet, γ is the current density (units A/m²) and f is a complex function defined by the integral (not shown). The on-axis $$H_z(z) = \frac{\gamma}{2} \int_0^L \log\left(1 + \sqrt{((z+q)/a)^2 + 1}\right) - 1\big/\sqrt{((z+q)/a)^2 + 1} - \log\left(\frac{z+q}{a}\right) dq = \frac{\gamma}{2} f(z/a) \quad (2)$$

magnetic force goes as $F_z \sim \partial(H_z^2)/\partial z$. Thus the magnetic force on the magnetic composition scales linearly with magnet size—doubling the size of the magnet doubles the focusing distance. Because the force goes as the magnetic field squared the scaling with respect to current density is better than linear—doubling the focusing distance requires increasing γ by $\sqrt{2}$. Scaling up the magnet size to a radius of a=10 cm and a length of L=3 cm achieves the same focusing force as in the experiment of Example 1, but at a distance of 30 cm with a 1.5 Tesla electromagnet—well below the ~4 Tesla value used in high-strength MR imaging. Increasing the strength of the magnets to 4 Tesla will allow a focusing force 6.7 times greater, per each such magnet, at a distance of 30 cm. As shown in FIGS. 6A and 6B, optimizing the shapes of the magnets 20 (e.g., shaped cone shown in FIG. 6B instead of a squat cylindrical as shown in FIG. 6A, both affixed to mountings 21 and 23) can yield further improvements.

When a dynamic magnetic field is used, changes in the magnetic field should not be made too rapidly in order to avoid undesirable physiological responses in the patient due to eddy currents. For example, rate of change (dB/dt) values of 60 Tesla/second are known to cause muscular twitches in the face and back along with uncomfortable "electric shock" sensations, hence the U.S. Food and Drug Administration (FDA) has recommended that dB/dt not exceed 20 Tesla/second. Accordingly, although the embodiments are not limited, it is preferred for use in medical applications with a living patient that the magnetic field be varied slowly at rates that are considered to be safe for medical use. In one embodiment, the rate of change (dB/dt) is less than about 80 Tesla/second, and more preferably less than about 70, 60, 55, 50, 45, 40, 35, 30, 25, 20, 15, or 10 Tesla/second. In a different embodiment, the rate of change (dB/dt) is less than about 25, 24, 23, 22, 21, 20, 19, 18, 17, 16, 15, 14, 13, 12, 11, 10, 9, 8, 7, 6, 5, 4, 3, 2, or 1 Tesla/second.

Likewise, the strength of the magnetic field that can be used is not limited, but for medical applications is generally desired to be no greater than about 8 Tesla for adults and 4 Tesla for children. Accordingly, although a magnetic field of any strength could be used, it is preferred for use in medical applications with a living patient that the magnetic field strength be no greater than about 10 Tesla, and more preferably no greater than 9.5, 9, 8.5, 8, 7.5, 7, 6.5, 6, 5.5, 5, 4.5, 4, 3.5, 3, 2.5, 2, 1.5, 1, 0.75, 0.5, 0.25, or 0.1 Tesla. In a preferred embodiment, the field strength is no greater than 2.5, 2.4, 2.3, 2.2, 2.1, 2.0, 1.9, 1.8, 1.7, 1.6, 1.5, 1.4, 1.3, 1.2, 1.1, 1.0, 0.9, 0.8, 0.7, 0.6, 0.5, 0.4, 0.3, 0.2, or 0.1 Tesla, and most preferably is less than about 1 Tesla. In a preferred embodiment, the rate of change is no greater than 20 Tesla/second, and a moderate field strength of 0.5 Tesla is used. This implies a bandwidth limitation of ≤40 Hz, although a weaker field can be traded for higher frequency.

B. Magnetizable Compositions

The magnetizable compositions comprise multiple magnetizable objects, e.g., a plurality of magnetizable nano-particles, such a plurality of particles comprising, for example, a ferrofluid—a suspension of magnetizable particles forming a magnetizable fluid. As used herein, the term "magnetizable" refers to the capability to become magnetized, and includes within its scope magnetic, paramagnetic, ferrous and diamagnetic. The magnetizable objects may have any suitable shape and composition, and are limited only by the need for them to be magnetically responsive and small enough to transport in the vasculature or other tissue. In various embodiments, the magnetizable objects comprise a therapeutic agent or a visualization agent, for therapeutic, prophylactic, and diagnostic uses.

The force per-unit-volume on the objects can be calculated on an object-by-object basis as per Equation 1. As is evident from Equation 1, the force on a ferrofluid equals the object concentration times the object volume, times the gradient of the magnetic field squared. Therefore, it can be seen that bigger objects under stronger magnetic fields, with higher gradients, will be easier to capture, although upper limits on object size are created by safety limitations placed on the magnetic field strength and temporal frequency. Magnetic spatial field gradients are limited by the engineering capability of accurately creating magnetic fields.

The object can be any size suitable for transport in living tissue or vasculature and capable of being focused magnetically. While larger objects are desirable to enhance magnetic manipulation (larger objects can be controlled with lower magnetic fields), objects over 600 nm in diameter may not be able to pass through cell pore membranes easily or at all or may be too quickly taken up by the bodies macrophage system and sequestered in the liver and/or spleen. In a preferred embodiment, the objects are small enough in size (less than about 250 nm diameter) to be able to diffuse into tissue and then enter cells (e.g., via endocytotic processes), while still being large enough (greater than about 100 nm diameter) to respond to the applied magnetic field.

In preferred embodiments, the magnetizable objects are nano-objects or micro-objects. As used herein, the term "micro-object" refers to an object having an average diameter of about 1 to 1000 μm, and the term "nano-object" refers to an object having an average diameter less than 1000 nm. In one embodiment, the magnetizable objects have an average diameter in the range of about 1 nm to 1 mm, preferably in the range of about 100 nm to about 200 nm, about 300 nm, about 400 nm or about 500 nm, or in the range of about 200 nm to about 300 nm, about 400 nm or about 500 nm, or in the range of about 300 nm to about 400 nm or about 500 nm, or in the range of about 400 nm to about 500 nm.

In a different embodiment, the magnetizable objects are micro-objects having an average diameter of less than about 250 μm, 200 μm, 150 μm, 100 μm, 75 μm, 50 μm, 25 μm, 20 μm, 15 μm, 10 μm, or 5 μm. In another embodiment, the magnetizable objects are nano-objects having an average diameter less than about 500 nm, 450 nm, 400 nm, 350 nm, 300 nm, 250 nm, 225 nm, 200 nm, 175 nm, 150 nm, 125 nm, 100 nm, 75 nm, 50 nm, 25 nm, 15 nm, 10 nm, 5 nm, or 1 nm. In yet another embodiment, the magnetizable objects are nano-objects having an average diameter in the range of about 1 to 500 nm, preferably in the range of about 25 to 400 nm, about 50 to 350 nm, about 60 to about 325 nm, about 75 to 300 nm, about 90 to 275 nm, about 100 to 250 nm, or about 125 to about 225 nm.

The magnetizable objects can be based on any biologically suitable material, and may take a variety of forms, such as liposomes, microspheres, nanospheres, micelles, vesicles, capsules, needles, or rods. The objects may be made out of any suitable biocompatible material such as chitosan, dextran, poly(lactic acid), starch, poly(vinyl alcohol), polyalkylcyanoacrylate, polyethylene imine, carbon, polysaccharides, heparin, gelatin, viral shells, or proteins. A magnetizable object may be a cell modified to contain or to be attached to a magnetizable material. The objects may have various coatings or attached substances, for example, a layer of carbohydrates may be attached to the objects in order to prevent aggregation (clumping) and a phosphate coating may be used to enhance in vivo residence time.

The magnetic responsiveness of the magnetizable objects may come from materials such as magnetite, iron, nickel, cobalt, neodymium-iron-boron, or samarium-cobalt, or any other material that reacts to a magnetic field. The magnetically responsive material may be biocompatible, may be non-biocompatible but coated with a biocompatible coating or layer, or may be non-biocompatible, for example a radioactive particle that is meant to cause tissue damage in order to effect radiotherapy. The magnetically responsive material may form an integral part of the object, for example a particle core or a nanorod coating, or may be attached to the object, for example attached to the surface. In one embodiment, the magnetizable objects comprise magnetite ($Fe_3O_4$), which has a magnetic susceptibility ($\chi$) of about 20, which is 5-7 orders of magnitude higher than the magnetic susceptibility of the body. In a different embodiment, the object has a core of magnetizable material such as iron oxide coated with carbohydrates linked to a therapeutic agent, for example epirubicin, mitoxantrone, or paclitaxel.

In a preferred embodiment, the magnetizable objects comprise a magnetically responsive core coated with a biocompatible material, which protects the magnetic material from the surrounding environment and can also facilitate functionalization by allowing the attachment of carboxyl groups, biotin, avidin, and other functional groups that can act as attachment points for therapeutic agents or targeting molecules.

In certain embodiments, the magnetizable objects are associated with a therapeutic agent (e.g., the therapeutic agent is entangled, embedded, incorporated, encapsulated, bound to the surface, or otherwise associated with the particle). In certain embodiments, the therapeutic agent is a drug such as a pure drug (e.g., drugs processed by crystallization or supercritical fluids), an encapsulated drug (e.g., polymers), a surface-associated drug (e.g., drugs that are adsorbed or bound to the object surface), or a complexed drug (e.g., drugs that are associated with the material used to form the object). In a different embodiment, the magnetizable objects exhibit fluorescent activity or a measurable signal when exposed to light or another external stimulus, which is useful for diagnostics, imaging and sensing.

The term "agent", as used herein, is thus intended to include compounds having utility for therapeutic and/or diagnostic and/or prophylactic purposes (e.g., therapeutic, diagnostic or prophylactic agents), and preferably therapeutic agents. Therapeutic agents include, e.g., antibiotics, antivirals, antifungals, anti-angiogenics, analgesics, anesthetics, anti-inflammatory agents including steroidal and non-steroidal anti-inflammatories (NSAIDs), corticosteroids, antihistamines, mydriatics, antineoplastics, immunosuppressive agents, anti-allergic agents, metalloproteinase inhibitors, tissue inhibitors of metalloproteinases (TIMPs), vascular endothelial growth factor (VEGF) inhibitors or antagonists or intraceptors, receptor antagonists, RNA aptamers, antibodies, hydroxamic acids and macrocyclic anti-succinate hydroxamate derivatives, nucleic acids, plasmids, siRNAs, vaccines, DNA binding (minor groove) compounds, hormones, vitamins, proteins, peptides, polypeptides and peptide-like therapeutic agents. Diagnostic agents include, e.g., dyes, contrast agents, fluorescent agents, radioisotopes (e.g., $^{32}P$, $^{99}TC$, $^{18}F$, $^{131}I$, etc.) and the like that are useful in the diagnosis of diseases, conditions, syndromes or symptoms thereof. A therapeutic agent administered in advance of the detection of a disease, condition, syndrome or symptom is a prophylactic agent.

The magnetizable composition may comprise a carrier fluid in addition to the magnetizable objects, for example an organic solvent or water, so that the magnetizable composition has the form of a ferrofluid. A ferrofluid, which is composed of many small magnetizable objects or particles, is effectively super-paramagnetic—it is strongly magnetized in the presence of an external field and is demagnetized as soon as the external field is removed due to rapid random particle reorientations.

C. Magnetism and the Body

Magnetic fields can be described using Maxwell's equations, and more specifically the magneto-static Equations (3) (magnetostatic equations are appropriate even for the dynamic magnetic fields discussed herein, because the field varies slowly compared to the timescales on which electric and magnetic fields interact), where B is the magnetic field (magnetic induction)

$$\nabla \cdot \vec{B} = 0 \text{ and } \nabla \times \vec{H} = \vec{j} \tag{3}$$

in Tesla, H is the magnetic field strength in Amperes/m, and j is the current density, in $A/m^2$. In a vacuum, $B=\mu_0 H$. In a material, $B=\mu_0(H+M)=\mu_0(H+\chi H)$ where M is the material magnetization. The human body consists of 80% water, along with other essentially non-magnetic materials (proteins, lipids, carbohydrates), and trace amounts of metals. As a result, magnetic fields are essentially unmodified as they pass through the body ($M_{body} \sim 0$; $\chi \sim 10^{-6}$ to $10^{-4}$). When injected, the magnetizable objects are conveyed by the blood stream, undergo diffusion within the blood, and are taken up and diffused through healthy and tumor cells inside the body. Human blood flow is up to 1.75 m/s in the ascending aorta, 40 to 70 cm/s in the cerebral arteries, and about 20 cm/s in main venus arteries. Blood velocity in secondary vessels including microvessels, which can be as small as 5 μm in diameter, may be as high as 1 mm/s. In blood vessels, the magnetizable objects will be carried along by the local blood flow velocity $V_{blood}$, with magnetic forces creating an additional velocity $V_r$ relative to the blood flow. This relative velocity is set by a competition between magnetic and drag forces on the particle. The Stokes drag on a spherical particle in a liquid is shown in Equation (4), where $\eta = 0.003$ N s/$m^2$ $$\vec{F}_{drag} = 6\pi a\eta \vec{V}_r \tag{4}$$

is the viscosity of blood. Setting Equations 4 and 1 equal, but per-particle (no C in Equation 1), gives the velocity of a single particle relative to blood flow as Equation (5):

$$\vec{V}_r = \frac{2a^2}{9\eta}\mu_0 \frac{\chi}{1+\chi/3} \nabla(\vec{H}^2) \tag{5}$$

This relative velocity is reached when the magnetic force on a particle is balanced by the blood drag force. For a 250 nm diameter particle in a 0.5 Tesla/cm magnetic gradient, this relative velocity will be $|V_r| \sim 30 \times 10^{-6}$ m/s=30 μm/s, which is small compared to the ~1 mm/s blood flow velocity of secondary and micro arteries, but still strong enough for magnetic forces to hold the objects against the blood flow. One reason for this is that blood flow is fast near the center of arteries, but slows to almost zero at the blood vessel walls. In macro vessels (>50 μm in diameter), blood acts essentially as a Newtonian fluid, having a roughly parabolic flow profile with maximum velocity at the center and zero velocity at the walls. Objects near the boundaries of the vessel see low blood flow velocities and can be captured by magnetic forces. Assuming such a parabolic flow profile and equating the maximum forces of Equation 1 versus the velocity dependent drag forces of Equation 4, the thickness of the magnetizable object capture region can be estimated. For a 1 mm diameter secondary blood vessel with a high 1 mm/s blood flow velocity, 250 nm diameter particles in a 0.5 T/cm magnetic gradient will be captured to a depth of ~7 μm. Hence, magnetizable objects are being concentrated in a thin layer at the blood vessel walls, which is highly desirable because the objects can then enter into vessel wall cells and migrate under the magnetic field to interior tissue cells.

Based on the above, the approximate governing partial differential equations for magnetizable object transport in blood vasculature are Equation (6), where C(x, t) is the $$\frac{\partial C}{\partial t} = -\nabla \cdot (-D\nabla C + \vec{V}C) \quad (6)$$

$$\vec{V} = \vec{V}_{blood} + \vec{V}_r = \vec{V}_{blood} + \frac{2a^2}{9\eta}\mu_0 \frac{\chi}{1+\chi/3}\overline{M}_{sat} \cdot \nabla \vec{H}$$

concentration of the magnetizable objects in 3D space and time [in number of moles/m³], D is the diffusion coefficient for objects in blood (small, probably negligible), V is the velocity of objects and is the sum of the local velocity of the blood $V_{blood}$ (large, pulsatile, varies in space and time) and the velocity $V_r$ due to the magnetic field gradient is as in Equation 5. This PDE is defined over a blood vasculature domain. As discussed, only near the blood vessel walls is $V_r$ comparable to $V_{blood}$, and so this is the region where magnetic control will likely actuate the magnetizable objects or ferrofluid.

For example, after being concentrated at the vessel walls in the vicinity of the tumor, the magnetizable objects are absorbed by the vessel wall cells. The mechanisms for this are not known in detail. Tumor cells generally have more porous membranes that can take up larger objects than non-tumor cells, but it is also known that cells can eject objects after having taken them up. Once the magnetizable objects are inside the cells, they will drift under the applied magnetic field, moving from cell to cell or between cells. Because every normal cell in the body is within about 100 μm of a blood vessel (about 5-20 cells distance), the remaining distance that must be covered by the magnetizable objects, from the blood vessel to the farthest tumor cells, is small. In contrast, as we have found during autopsies, metastatic cancer cells may be further removed from blood vessels, and this necessitates the sweep methods. Thus, in this version of the magnetic control, the magnetizable objects are controlled close to tumor regions inside the blood. Sweeping can then be used to move them to metastatic cells if these cells are further away from blood vessels. Sweep transport of ferrofluid is possible through other channels, e.g. through tissue, through interstitial fluid, the lymphatic system, through tissue air gaps, through the gut, as well as through available vasculature as described above.

The in-tissue analog of Equation 6 for magnetizable object transport through cells surrounding the blood vessels is Equation (7):

$$\frac{\partial C}{\partial t} = -\nabla \cdot (-D\nabla C + \vec{V}C) \quad (7)$$

$$\vec{V} = k\mu_0\overline{M}_{sat} \cdot \nabla \vec{H}$$

where k is the mobility coefficient for magnetizable objects through tissue (from cell to cell and between cells). This PDE is defined over the tissue surrounding a blood vasculature domain. Here, outside the blood vessels, the magnetic field forces no longer need to compete against large blood forces, but instead compete mainly against diffusion.

Applying these principles to the systems and methods of the present embodiments, it is evident that a magnetic field may be dynamically manipulated in order to direct magnetizable objects to particular regions in a patient's body, even deep targets within the body such as the lungs, intestines, or liver. As previously mentioned it may also be used to direct ferrofluid to a target volume region or to sweep from one volume to another. In preferred embodiments, the target volume contains regions at least 5 cm, 10 cm, 15 cm, 20 cm, 25 cm, or more than 30 cm within the body. As is evident from the foregoing discussion, the directing or containment of the magnetizable objects can be evaluated either at an instant in time, or on average over a time period.

It is also understood that containment is relative, and that it is not necessary to contain 100 percent of the administered objects in order for effective treatment. Conventional methods of administering chemotherapy currently deliver less than about 0.1 percent of chemotherapeutic agents to the target volume. In a preferred embodiment, at least 0.1 percent, 1 percent, 5 percent, 10 percent, 50 percent, or 95 percent of the administered magnetizable objects are contained, or moved through the target volume to be treated. In a different preferred embodiment, the more of the administered magnetizable objects are delivered to the target volume than in conventional chemotherapeutic methods, e.g., 1.1 times the standard amount (about 0.1 percent) of chemotherapeutic agents to the target volume, or 1.5 times, 2 times, 3 times, 4 times, 5 times, 6 times, 7 times, 8 times, 9 times, 10 times, 100 times, 1000 times, or more than 1000 times the standard amount to the target volume.

It is understood that the magnetic control can be shaped in time, in space, or in both. It is further understood that magnetic control can be used to achieve just a portion of the desired ferrofluid control, both for regional targeting and for sweeping. For example, if natural processes inside the human body tend to move the magnetizable objects to well vascularized portions of the liver, and the need is to target poorly vascularized metastases within the liver, then the magnetic field is not necessary to target to the first volume. Here a simple sequence of control actions, such as shown in FIG. 12, can then be used to sweep ferrofluid from the liver into all, or the majority of, the poorly vascularized metastases. In this case, magnetic control is only required for the sweeping, it is not required for the first step of directing the ferrofluid to the desired surrounding first volume.

D. Feedback Control Algorithm Design

Magnet control, and more specifically feedback control, in the embodiments is governed by a control algorithm, which decides what magnet to actuate when and for how long in order to contain or move the magnetizable objects in the body. Control is complicated both because shaping the magnetic field in space and time can be complex (as evidenced by FIG. 8) and because inside a patient many factors are unknown (such as his/her vascular geometry, blood flow, and rates of object uptake from blood to tissue) but some factors are known. The magnetic fields applied to the body are known, as are the magnetic forces that they generate on the magnetizable objects. Any suitable control algorithms may be used to control feedback. In one, non-limiting, embodiment we use a quadratic programming optimization control.

Non-limiting examples of control algorithms used in a preferred embodiment are based on the mathematical model of Equation (8), where C is the concentration of nanoparticles $$\frac{\partial}{\partial t} C(\vec{r}, t) = \qquad (8)$$
$$-\nabla \cdot \left[ C(\vec{r}, t) \vec{V}_{blood}(\vec{r}, t) - D(\vec{r}) \nabla C(\vec{r}, t) + k(\vec{r}) C(\vec{r}, t) \nabla \left( |\vec{H}(\vec{r}, t)|^2 \right) \right]$$

in the body as a function of time t and space r=(x, y, z). C can be measured fully or in part using a sensor system as previously described, for example a gamma ray camera or a PET scanner. Although the following discussion refers to nanoparticles, the invention is not so limited. $V_{blood}$ is the blood convection, D is the diffusion, k is the magnetic drift coefficient, and $\nabla(|H|^2)$ is the control.

The rate of change of the nanoparticle concentration is given by the gradient ∇ of the flux. The flux is composed of 3 terms. First, transport of particles by the blood flow velocity $V_{blood}$. The velocity of blood is high in some regions, it varies from person to person, is pulsatile, and currently it is not feasible to measure it for each patient. Second, in addition to being carried by the blood, the nanoparticles diffuse within the blood stream. For spherical nanoparticles in blood at body temperature, Brownian diffusion can be calculated by Einstein's law, but red blood cell collisions may further scatter the particles and this scattering can be modeled as additional diffusion. The effect is greatest at the blood vessel walls where the blood shear is highest and it makes the diffusion coefficient D a patient-specific function of space r. Third, the applied magnetic field creates a velocity of the nanoparticles relative to the blood flow, a magnetic drift. Its size is determined by the balance between the applied magnetic force and the opposing viscous forces (Stokes drag) in the blood. The resulting coefficient is $k=(a^2/9\eta)\mu_0 \chi/(1+\chi/3)$ where η is the viscosity of blood and a, $\mu_0$, and χ are as defined for Equation 1. However, blood Stokes drag on a spherical particle increases when it is near the blood vessel wall due to edge effects and this makes k a function of space. Magnetic fields are essentially unaffected by tissue and so the $\nabla H^2$ term is known precisely, even inside the body. Here the convection, diffusion, and magnetic drift of the nanoparticles occurs inside a vasculature network geometry, which varies greatly from person to person.

Vascular variation may be accounted for in the control algorithm, for example by using expert knowledge on difference of vasculature in different regions (e.g. brain vs. legs), by measuring individualized blood flow velocities, or mapping individual vasculature geometries to a degree allowed by, for e.g., magnetic resonance imaging, and therefore control algorithms can be selected, or customized, for specific locations within a patient (e.g. for lung vs. head and neck targeting) or for individual patients or groups of patients.

During feedback control, the control goal is to manipulate the last term of Equation 8 to correct for nanoparticle location errors caused by the diffusion term and the blood convection terms in the smaller blood vessels. It is not possible to correct for blood flow forces at the center of main arteries and veins, the flow there is too strong. Our control algorithm uses this third term to increase particle concentration at the deep tumor location whenever possible: it does not require knowledge of blood vasculature geometry or blood flow distribution in each patient. Feedback (correcting actuation based on real-time sensing) may or may not be necessary depending on the situation. To sweep poorly vascularized metastases in the liver (for example as shown in FIG. 12) it is likely not necessary as a planned sequence of sweep steps will suffice. To target a specific target whole volume including all locations within that volume, feedback may allow dramatic improvement in performance.

An optimization problem whose solution will determine the magnetic field that is applied to focus the nanoparticles at each moment in time is now defined. If the desired target volume is quantified by a weight W (W is set high in the volume, is low outside it), then the degree of nanoparticle targeting achieved at time t is quantified by the cost, as shown in Equation (9)

$$J(t) = \int C(\vec{r}, t) W(\vec{r}) d\vec{r} \qquad (9)$$

where C is the concentration of the nanoparticles, W is a weight that is large inside the target volume and is small elsewhere, and the integral is over a body volume that contains the tumor target. This cost J is high if the nanoparticles are concentrated in the target volume and is small otherwise. The control goal is to maximize the cost J. Differentiating Equation 9, and using Equation 8, the time rate of change of this cost is given by Equation (10), where the integral $$\frac{\partial J}{\partial t} = \int \frac{\partial C}{\partial t} W d\vec{r} = \int \left[ -\nabla \cdot (C \vec{V}_{blood}) + \nabla \cdot (D \nabla C) \right] W d\vec{r} - \qquad (10)$$
$$k \int \left[ \nabla C \cdot \nabla \vec{H}^2 + C \nabla^2 \vec{H}^2 \right] W d\vec{r}$$

was split, the chain rule used on the control term, and k was treated as constant. The last 2 terms correct for nanoparticle position errors cased by the first two terms, diffusion and blood convection, on the right hand side.

Thus H must be optimally chosen to best focus all, or a majority of or a fraction of, the ferrofluid using N stationary electromagnets whose strength can be dynamically controlled. At unit strength, the jth magnet will create a magnetic field $H_j(r)$. By the linearity of Maxwell's equations (3), if at time t all N magnets are actuated at strengths $u(t)=[u_1(t), u_2(t), \ldots, u_N(t)]$, then the net resulting magnetic field is calculated by Equation (11):

$$\vec{H}(\vec{r}, t) = \sum_{j=1}^{N} u_j(t) \vec{H}_j(\vec{r}) \qquad (11)$$

Substituting 11 into 10, expanding the square, and rearranging the integral yields Equation (12):

$$\frac{\partial J}{\partial t} = \int \left[ -\nabla \cdot (C \vec{V}_{blood}) + \nabla \cdot (D \nabla C) \right] W d\vec{r} - k \int W \nabla C \cdot \nabla \qquad (12)$$
$$\left( \sum u_j \vec{H}_j \right)^2 + W C \nabla^2 \left( \sum u_j \vec{H}_j \right)^2 d\vec{r}$$
$$= \ldots - k \sum_{i=1}^{N} \sum_{j=1}^{N} u_i \underbrace{\left[ \int W \nabla C \cdot \nabla (\vec{H}_i \cdot \vec{H}_j) d\vec{r} + \right.}_{Aij}$$

$$\underbrace{\int WC\nabla^2(\vec{H}_i \cdot \vec{H}_j) d\vec{r}}_{B_{ij}} \bigg| u_j$$

$$= \ldots - k\vec{u}^T[A+B]\vec{u}$$

In the second line only the control term is written, the other terms are marked by dots. In the second line, $A_{ij}$ is the first integral, and $B_{ij}$ is the second. The matrices A and B, with integral entries $A_{ij}$, $B_{ij}$, can be quickly computed at each new time (only C changes): the weight W was chosen, nanoparticle concentration C is being measured, and the magnetic fields $H_i$ and $H_j$ are accurately known from simulation. The control $u(t)=[u_1(t), u_2(t), \ldots, u_N(t)]$ makes $-ku^T[A+B]u$ as positive as possible so that it increases focusing metric J as much as possible.

This same scheme can be adapted to achieve optimal sweeping. Here the weight W now reflects the second desired volume. The optimization will now shape the magnetic field to best direct the magnetizable objects (ferrofluid) from where they are now into the desired second volume—it will sweep in the ferrofluid. As noted earlier, sweep can be simpler to implement and may not require real-time sensing. Sweep can, however, still benefit from an optimization similar to the above even in the absence of real-time sensing (feedback).

Safety constraints can be imposed on the magnetic fields as hard bounds (no control action will exceed them). For example, from Equation 11, using a 4 Tesla limit for children, a quadratic constraint on the control action u is given by Equation (13):

$$|\vec{H}|^2 = \vec{H}(\vec{x},t) \cdot \vec{H}(\vec{x},t) = \Sigma\Sigma u_i u_j \vec{H}_i \cdot \vec{H}_j \leq (4T/\mu_0)^2 \quad (13)$$

The FDA safety limit on the rate of change (20 T/s) can be used as another quadratic constraint on the change in control, which, from the prior known value of the control translates into a quadratic constraint on u. These limits on magnetic field strength and rate of change will still allow deep tissue (~30 cm) focusing. Magnetic nanoparticles are likely being focused primarily in micro-capillaries and at vessel walls where the blood velocity is slow, so extremely fast magnetic field actuation is not required. This constraint still allows a strong, say 3 T, stationary baseline field with significant on-top modulation of ±1T at 20 Hz—a strong modulation 20 times faster than the resting heart rate.

Maximization of deep nanoparticle focusing $-ku^T[A+B]u$ is thus, in this preferred embodiment, a quadratic cost problem with quadratic constraints. This is a standard optimization problem, in this case a small problem (its dimension is equal to the number of electromagnets, N, which will typically be few in number compared to the size of common optimization problems), and it can be solved quickly (between control updates). The focusing metric is improved whenever the optimal control term can direct the magnetizable objects (here magnetic nanoparticles) to the target volume, or to sweep them, more than the diffusion and convection terms defocus them. This control algorithm does not require measurement or knowledge of patient-specific vasculature geometry or blood flow velocities. Whenever it is possible to improve the concentration of nanoparticles at the target volume or sweep target by choosing a magnetic field, this optimization will do so.

Having now generally described the invention, the same will be more readily understood through reference to the following examples, which are provided by way of illustration and are not intended to be limiting of the present invention unless specified.

EXAMPLE 1

Saddle Motion Control at Blood Vessel Walls

FIG. 3 illustrates the saddle motion control of ferrofluid in a blood vasculature network. The magnetic field is strongest along the magnet axis 24 and the ferrofluid will flow to this axis along the inside of blood vessel walls. Once near the axis, the particles will flow toward the nearest or strongest magnet. By varying magnet strength and positioning the saddle on either side of the majority of the ferrofluid, the ferrofluid can be shuttled between magnets to focus, on average, to the tumor location 120.

Focusing in two dimensions perpendicular to the axis between the magnets is passive: the highest magnetic field is along the axis and so the magnetic forces point in toward the centerline. These passive forces will move the particles toward this axis along the inside blood vessel walls irrespective of the precise shape of the vasculature network. To further improve focusing with respect to the unknown vascular geometry, it is possible to swivel the magnet axis to move the ferrofluid out of local vasculature pockets.

To control the ferrofluid along the magnet axis, the strength of the two opposing magnets will be slowly changed to position the saddle equilibrium point on one side or the other of the majority of the ferrofluid, to continuously move it back toward the tumor, as shown in FIG. 3. For example, if the ferrofluid center-of-mass along the magnet axis is to the left of the tumor, magnet strengths will be chosen to position the saddle to the left of this ferrofluid center (left magnet weak, right magnet strong), which will push fluid back right toward the right magnet and tumor along the complex topology of the inside surface of the vasculature network.

EXAMPLE 2

Control of a Single Droplet of Ferrofluid

Control of a single droplet of ferrofluid along arbitrary paths, far away from all control magnets, has been demonstrated in the experiment shown in FIG. 13. In this experiment the ferrofluid droplet was controlled along a 'UMD' path (for University of Maryland) in the center of the experiment. The magnetic field was shaped in time and space to achieve this control. Every time the ferrofluid droplet was to the North of its desired location, the South magnet was turned on; if it was to the East of its desired location, the West magnet was turned on to an appropriate strength (computed by the model above). This experiment demonstrates that dynamic shaping of the magnetic field can control a collection of magnetic nanoparticles along an arbitrary path deep between magnets.

EXAMPLE 3

Electromagnet Control and Sensing

We now describe a further experiment. The ability to control and sense magnetizable nanoparticles in a ferrofluid at distances greater than 30 cm will be confirmed via the following procedure. The required stronger (~1.5 Tesla) magnets will be custom made from microbore copper piping (to allow in-situ water cooling) wound onto an appropriate core. The magnets will be driven by high-quality high-current kW power suppliers and amplifiers. A quiescent blood-mimic fluid such as that described by K V Ramnarine et al. (1998) Ultrasound in Medicine & Biology 24:451-459 (85% distilled water, 10% glycerol, 5% other additives) will be inside a clear 0.5 m on a side cubic container placed between sets of electromagnets. More than one magnet is needed to combat diffusion and buoyancy forces. A commercially available ferrofluid from Chemicell (Berlin, Germany) will be used that is composed of 250 nm diameter magnetizable particles.

Two, then six electromagnets, spaced 0.6 m apart, will be dynamically controlled to focus the ferrofluid. Focusing will occur on the magnet axis to any desired vertical location, such that the ferrofluid concentration is increased 100:1 as compared to background in a <1 cm diameter target region. The location of the ferrofluid inside this vessel will be imaged in real-time by two (or three) orthogonal cameras. A suitably fast frame-grabber will gather images from all the cameras at once, and in-house imaging algorithms will then be used to infer the position of the ferrofluid. If the applied magnetic field adversely impacts the function of the cameras (unlikely), then the cameras can be shielded or can be fed by optical fibers (so optics to fibers to camera imaging hardware) so that the cameras are completely protected.

The quadratic programming control algorithms discussed earlier can be adapted to achieve this case.

EXAMPLE 4

Electromagnet Control and Sensing in 3D Vasculature Models

During treatment, drug-coated nanoparticles are injected into a vein. Hence one approach to deep tissue focusing is to first achieve focusing within the vasculature, before extravasation in the target vicinity, diffusion and magnetic drift (intra and extra cellular), and cell uptake can deliver a portion of the focused chemotherapy drugs to tumor cells.

Blood flow carries the nanoparticles along and the magnetic field is used to stop and concentrate them. Even with a high magnetic field gradient, the magnetic forces are small compared to blood convection (particle drag) forces in major vessels. Only those particles in slow moving blood can be stopped. For example, for 250 nm particles with a moderate 1 T/cm magnetic field gradient at the target location, the particles can be stopped if the surrounding blood flow is <0.12 mm/s Inside the body, blood flow velocities range from the very high (>1 m/s highest peak velocity in the ascending aorta) to ~30 cm/s in main blood return venus arteries to <5 mm/s in capillaries and venules. Yet 1 T/cm magnetic field gradients can capture and effectively concentrate particles, because the flow profile of blood in vessels is approximately parabolic, i.e., it is maximum at the vessel centerline and is low at the vessel walls due to viscous shear forces. Magnetic forces are strong enough to capture the nanoparticles in a thin boundary layer at the surface of minor blood vessels where the blood flow velocity is low. It is this thin, slow moving, coating of ferrofluid at the inside surface of the vasculature that must be controlled and concentrated.

To achieve these goals, the container of Example 3 will be replaced by a series of vasculature phantoms. Blood-mimic flow in these phantoms will be driven by a heart mimic pump (Shelley Medical Systems, London, Ontario). The electromagnet control algorithm describing how to actuate the magnets so that they focus the ferrofluid inside the vasculature network is based on the mathematical models previously described, with reference to Equation 8. The phantoms will use the blood-mimic fluid described by Ramnarine et al. (85% distilled water, 10% glycerol, 5% other additives) because it has the same approximate viscosity and density as blood. A heart pump mimic (Shelley Medical Systems) will drive the fluid.

The cameras will locate the position and shape of the ferrofluid inside the transparent vasculature phantoms, in real-time. Each camera will first take a photograph of the experimental setup without any of the ferrofluid. During the experiment, these nominal images will be subtracted away from the current images, thus identifying only those pixels that have changed—the ferrofluid. Real-time filtering, smoothing, and registration algorithms will be created to identify the location and shape of the ferrofluid in the phantom, as described by M. Armani et al. (2005) Int'l J. of Robust & Nonlinear Control 15:785-803 and I. Triese et al. (2004) Lab on a Chip 5:285-297. Image darkness correlates to local ferrofluid concentration. Light intensity will be measured against ferrofluid concentration, for a range of well-mixed ferrofluid concentrations in blood-mimic fluid under controlled light conditions, to provide a diagnostic curve of concentration vs. intensity. This curve will then be used to quantify the amount of ferrofluid focusing achieved during feedback control experiments.

Vasculature phantoms will proceed from simple to more advanced. The first phantom will be a transparent porous PDMS network. Polydimethylsiloxane is a clear plastic whose porosity can be controlled by preparation. Other transparent gels or plastics with different network properties can also be used. The purpose in this first 'phantom' is simply to introduce a network, so that ferrofluid focusing can be tested inside it. Spaced magnets will be used, with a ferrofluid comprising 250 nm diameter particles. Focusing will occur such that the ferrofluid concentration is increased as compared to background in a target region. The blood mimic fluid is quiescent in this phantom.

The next phantom will be a more accurate representation of human vasculature. It is possible to fabricate phantoms from computer representations of vasculature, for example as described by C P Renaudin et al. (1994) Radiology 190(2): 579-582 and Y. Zhang et al. (2007) Computer Methods in Applied Mechanics and Engineering. Here, a computer aided manufacturing technique (e.g., stereolithography) is used to make a copy in plastic of a computer representation of the vasculature, as derived from MR imaging or the visible human project. Phantom resolution is set by the accuracy of measuring the vessels (e.g., the 1 mm spacing of slices in the visible human project), the resolution of the computer drawing reconstruction, and the spatial resolution of the fabrication process. Phantoms that will replicate human vasculature to ~1 mm accuracy are achievable using these methods. Six to 10 electromagnets will focus 250 nm particles inside the phantom. With quiescent blood-mimic fluid, focusing will occur such that the ferrofluid concentration is increased as compared to background in a target region. The heart-pump will also be used to mimic various physiological conditions of blood flow, under which conditions focusing will occur such that the ferrofluid concentration is increased as compared to background in a target region.

The third phantom will be an inverse mold from real-body plastination specimens, which has the advantages of having micro-capillaries, in addition to the major veins and arteries above. Inverse molds of vasculature specimens that include micro-capillaries will be created using molds around the specimens, and then dissolving them out with acid. The result will be a mold that is clear plastic where tissue was and air where blood was. Different representative vasculatures will be used, beginning with head and neck vasculatures. Six to 10 electromagnets will focus 250 nm particles inside the phantom with the heart-pump used to mimic various physiological conditions of blood flow, under which conditions focusing will occur such that the ferrofluid concentration is increased as compared to background in a target region.

EXAMPLE 5

Dynamic Control of Magnetic Fields: Focusing Magnetic Carriers to Targets Deep Inside the Body Background: A limitation in prior magnetic drug delivery efforts lay in the inability to focus treatment to targets deep inside the body. When stationary external magnets are used they attract the particles and can only concentrate them near the skin surface—magnets of a maximum safe strength can only create a <5 cm deep focus (Voltairas, P A et al. (2002) Journal of Biomechanics 35:813-821; Grief, A D et al. (2005) J. of Magnetism and Magnetic Materials, 293:455-463; Hafeli, U O et al. (2007) J. of Magnetism and Magnetic Materials, 311:323-329). This is a well-known and well-recognized problem. It is a fundamental consequence of the classic Samuel Earnshaw 1842 theorem (Earnshaw, S. (1842) Trans. Camb. Phil. Soc., 7:97-112). This theorem states that no inverse-square law force (which includes magnetic forces on a single particle) can create a stable trap in the interior. With a static magnetic field, only unstable equilibria are possible for a ferro- or para-magnetic particle.

Earnshaw's theorem can be bypassed in three ways. First, magnets or magnetic materials, such as magnetic stents or magnetizable wires or needles, can be implanted inside the body to create a local magnetic field maximum and attract particles to them (Iacob, G H et al. (2004) J. Optoelectronics and Advanced Materials 6:713-717; Ritter, J A et al. (2003) Abstracts of Papers of the American Chemical Society 225 (2003) U991; Iacob, G H et al. (2004) Biorheology 41:599-612; Avilés, M O et al. (2005) J. Magnetism and Magnetic Materials 293:605-615; Rosengart, A J et al. (2005) J. Magnetism and Magnetic Materials 293:633-638; Rotariu, O. et al. (2005) J. Magnetism and Magnetic Materials, 293:639-647; Yellen, B B et al. (2005) J. Magnetism and Magnetic Materials, 293:647-654). Surgically implanting such objects in a patient can be undesirable and is not always possible in a clinical setting. Second, the walls of a container can hold particles away from a magnet: a magnet can trap magnetic carriers against a perpendicular confining wall. But the human blood vasculature network is not a collection of simple, conveniently oriented, confining vessels and, as we see in the animal and human clinical trials of our collaborator (Lubbe, A S et al. (1996) Cancer Res., 56:4694-4701; Lubbe, A S et al. (1996) Cancer Res. 56:4686-4693; Lemke, M I et al. (2004) Eur. Radiology 14:1949-1955), magnetic carriers spill out from one blood vessel to the next to collect at vessels closest to the external magnet. A final way to bypass the theorem is to change the applied magnetic fields in time, and this is the approach taken in the embodiments which dynamically manipulate magnetic fields to focus magnetic carriers to deep targets.

The work of Potts and Diver (Potts, H E et al. (2001) J. of Physics D-Applied Physics 34:2629-2636), shows that dynamic control of just a single electromagnet can bypass Earnshaw's theorem: it can hold a drop of ferrofluid (nanoparticles in suspension) at a distance from the magnet. The drop is held together by surface tension so the control is effectively that of a single object: if the drop is too low it is brought back up and vice-versa. Magnetic manipulation of single objects in-vivo by feedback control has been demonstrated by Martel, who has shown steering of one micro particle at a time in swine vasculature using an MRI machine (Martel, S. et al. (2007) Applied Physics Letters 90:114105; Mathieu, J B et al. (2007) Biomedical Microdevices, 9:801-808), and by the company Stereotaxis who precisely controls magnetic fields to help guide surgical tools for magnetically assisted surgery (Ritter, R C (U.S. Pat. No. 6,241,671)) their instruments have achieved >10,000 successful heart surgeries.

During existing magnetic chemotherapy treatment, which has gone through phase I human trials for shallow tumors (Lubbe et al.; Lemke et al.) in Germany, the location of advanced and unsuccessfully pretreated cancers or sarcomas is known, a ferrofluid consisting of nano-particles coated with a chemotherapy drug (e.g. mitoxantrone or epirubicin) is injected into a vein, is circulated by the blood flow, and external magnets must then focus it to tumor locations. Thus it is necessary to concentrate a distributed ferrofluid to targets. This is more difficult than magnetically manipulating the location of a single object (as is done in all 3 examples above). Below data is presented demonstrating that dynamic magnetic actuation can still bypass Earnshaw's theorem for a distributed ferrofluid and enable its focusing to deep targets. Initial control results are presented along with a discussion of real-time ferrofluid sensing and feedback control.

Modeling: To rationally design dynamic actuation to focus a ferrofluid to deep targets, a mathematical model of how time-varying actuation will transport the fluid is employed. The model developed and implemented herein is the simplest one that contains the essential features: dynamic magnetic actuation and the resulting ferrofluid transport.

This model is similar to the one in Grief et al. with the difference that we have gone beyond analytical solutions for simple cases and implemented ours numerically (in COMSOL):

$$\nabla \cdot \vec{B} = 0 \text{ and } \nabla \times \vec{H} = \vec{j} \quad (3)$$

$$\frac{\partial}{\partial t}\underbrace{C(\vec{r}, t)}_{\text{Ferrofluid Concentration}} = -\nabla \cdot \left[ C(\vec{r}, t) \underbrace{\vec{V}_{blood}(\vec{r}, t)}_{\text{Blood Convection}} - \underbrace{D(\vec{r})}_{\text{Diffusion}} \nabla C(\vec{r}, t) + \underbrace{k(\vec{r})}_{\text{Magnetic Drift Coefficient}} C(\vec{r}, t) \nabla (\underbrace{|\vec{H}(\vec{r}, t)|^2}_{\text{Control}}) \right] \quad (8)$$

Equation (3), the magneto-static version of Maxwell's equations is appropriate: the employed actuation will be quasi-steady compared to radio frequencies. Here B is the magnetic field [in Tesla] with $B = \mu_0(H+M) = \mu_0(H+\chi H)$ where M is the material magnetization, H is the magnetic intensity [Amperes/meter], $\chi$ is the magnetic susceptibility of the particles (non-dimensional), and j is the current density [A/m$^2$] within the electromagnets.

In Equation (8), C is the concentration of ferrofluid in the body as a function of time t and space $\vec{r} = (x,y,z)$. The rate of change of this concentration is given by the gradient $\nabla$ of the flux which has three terms: 1) Convection of particles by the blood flow Velocity $V_{blood}$; 2) Diffusion of the particles within the blood stream. For spherical nanoparticles in blood at body temperature, Brownian diffusion can be calculated by Einstein's law, but, as noted by Grief, red blood cell collisions serve to further scatter the particles, and this scattering can be modeled as additional diffusion. 3) Magnetic drift. The applied magnetic field $H(\vec{r}, t)$ creates an additional velocity of the nanoparticles relative to the blood flow. Its size is determined by the balance between the applied magnetic force and the opposing viscous forces: the coefficient is: $k=(a^2/9\eta)\mu_0\chi/(1+\chi/3)$ where a is radius of the particles, $\eta$ is the viscosity of blood, $\mu_0=4\pi\times10^{-7}$ Vs/A m is the permittivity of vacuum, and H is the externally applied magnetic field intensity. The k coefficient is treated as a constant even though it can vary due to Stokes drag wall effects (slightly higher drag near blood vessel walls) and potentially due to some amount of particle chaining or aggregation (typically not seen to be significant in Luebbe's animal and human trials, thus Equation (8) does not yet include microscopic agglomeration forces).

As written, the model of Equation (8) is for transport within the vasculature. In surrounding tissue there would be an equivalent partial differential equation without blood convection terms and with different (lower) effective diffusion coefficients (W M Saltzman (2001) DRUG DELIVERY: ENGINEERING PRINCIPLES FOR DRUG THERAPY, Oxford Univ. Press, USA). There would also be an extravasation term that described ferrofluid transport from blood to surrounding tissue. This level of detail also has not yet been included in the modeling.

This model is currently implemented in 2 spatial dimensions in COMSOL via a Matlab script that allows inclusion of feedback control—it allows magnetic actuation to be set by control algorithms that have access to the ferrofluid distribution at each time. The magneto-static equations are written in vector potential form and the convection-diffusion equation is in conservative weak form and contains a small amount of Petrov-Gallerkin streamline diffusion to prevent numerical instabilities. Both are solved simultaneously using $6^{th}$ order Lagrange-cubic finite elements. The model can handle any time-varying control inputs, pre-planned or due to closed-loop feedback control, but it smoothes out sharp jumps in time, such as suddenly turning on a magnet, over a small interval. Typically, the model has ~3,000 mesh points and runs in minutes to a few hours on a personal computer (depending on the complexity of the control algorithm). For the control case below the model is solved in non-dimensional parameters and there is no blood flow velocity yet ($V_{blood}=0$) since the goal is to demonstrate the ability to focus a distributed ferrofluid without any disturbances due to convection.

Figure 9:
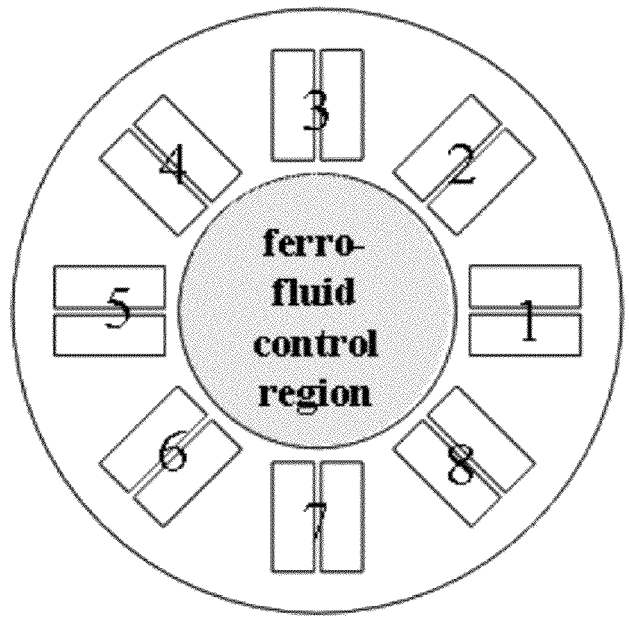
FIG. 9 shows a preferred model setup. Equation (3) is solved everywhere in the simulation domain which includes the 8 controlled magnets and an inner domain where ferrofluid transport takes place (Equation (3) and (8)).

Non-dimensional parameters for the simulation were set at diffusion D=1 and magnetic drift coefficient k=1000 with initial conditions C(x,y,0)=1. The eight magnets (FIG. 9) were spaced out equally at a radius of 1.5 (origin to center of each magnet) had a length of 0.8 and a width of 0.35 (0.15 for each half of the coil with a 0.05 gap). The electro-magnets were actuated by imposing opposing vertical currents through the two coil halves: in FIG. 8 an inward arrow −1 actuation means that the half-coil in the clockwise direction had a −1 (down) current and the other coil had a +1 (up) current; vice versa for a reversed polarity (outward +1) actuation. For numerical stability, the compensated Petrov-Galerkin streamline diffusion parameter was $\delta_{SD}=0.5$.

Magnetic Control: FIG. 8, Panel A shows the response of the ferrofluid to a single magnet that is turned on and left on. This simulation begins with a uniform ferrofluid concentration at time zero: C(x,y,0)=1. Fluid moves towards the highest magnetic field amplitude squared (to the maximum of $H^2$) and collects as close to this maximum as possible. If all 8 magnets were turned on and left on, the ferrofluid would collect at 8 spots nearest to the 8 magnets. This would also create a transient hot spot at the center since fluid there would be removed last. Creating such a "focus" by depleting ferrofluid everywhere else is not a viable in-vivo targeting approach since blood flow would quickly wash away this remaining region of the ferrofluid. Instead, our goal is to actively move ferrofluid to the deep target.

Application of the first dynamic control algorithm is shown in FIG. 8, Panel B. At time t=0, the y-axis magnets (3rd and 7th) are turned on along the same direction (i.e. opposite polarity in the convention of FIG. 8) with unit strength. This creates the highest magnetic field along the y axis, and along this axis, the field is highest nearest the two on magnets. The resulting magnetic energy surface is a saddle, as shown in FIG. 8, Panel B, Subpanel i (bottom). Fluid flows down this saddle: it forms a transient hot-spot at the center (where depletion is slowest) and collects near the two on magnets.

The key challenge now is to get the ferrofluid out from near the two y-axis magnets and moving towards the center. To do so, at time t=4, the 8 magnets are switched to values u=[+1,+0.3,0,−0.3,−1,−0.3,0,+0.3] as shown in FIG. 8, Panel B, Subpanel ii. The extra |0.3| values of magnets 2, 4, 6, and 8 create two local unstable (energy maxima) along the axis just outside the ferrofluid hot spots (see the force arrow sources in FIG. 8, Panel B, Subpanel ii adjacent to magnets 3 and 7) and they cause the ferrofluid to spill down the energy surface towards the center target.

Ferrofluid continues to move in along the y axis but by t=9 there is a significant amount of spreading out along the x direction, towards magnets 1 and 5 (looking at the energy surface in FIG. 8, Panel B, Subpanel iii, it is visible how the ferrofluid hot spot is on a surface that is curved along the x direction). To combat this, magnets 2, 4, 6 and 8 are turned on to higher values (this switch from |0.3| to |0.5| happens smoothly from t=8.9 until t=9.1) which flattens out the energy surface in x somewhat (FIG. 8, Panel B, Subpanel iv) limiting further spread in x but continuing to drive the fluid in along y.

By t=14.1, the ferrofluid hot spot has reached the center target but has nevertheless spread significantly in x. The x axis magnets 1 and 5 are now turned on, at t=14, to create foci near those magnets. The sequence then repeats in the x direction: place saddles outside the foci to drive them back in (t=20) and flatten the energy surface in the y direction at t=25 to limit spreading in the y direction. The results, both in terms of ferrofluid concentration and the energy surface are 90 degree flips of those already shown in the y direction. As this sequence repeats the control scheme continually drives ferrofluid through the center thus creating a hot spot on average at the central target (as shown in FIG. 8, Panel C).

This control algorithm was chosen by hand and may be further optimized. For example, optimization problems may be phrased to optimize each step (shape foci at edges, move to center, prevent spread in other directions, repeat). For example, maximizing fluid transport from a current hot spot to a neighboring target region or way point, the move problem, can be cast as a quadratic optimization program. Instead of choosing values for the side-magnets (2, 4, 6, and 8 above) by hand to flatten out a region, the magnet values may be optimally chosen. It is also clear how the control schemes can be extended to deal with a disturbing convective flow. Energy surfaces can be shaped and re-oriented to bring the fluid back as it is disturbed. More sophisticated control schemes will correct the location of hot spots and also refocus them. For example, initial optimization results show that it is possible to move and shorten hot spots along their longest axes—by placing energy maxima or saddles behind them to cause the tail end to catch up with the front end.

The In Vivo Problem: The in-vivo deep-target control problem has more factors than those addressed in the starting simulations and initial control scheme above. Although the mathematics of the control problem (focusing a distributed fluid to an internal target) is non-standard and difficult and there are no existing control methodologies, the principles of the present invention enable the direction and guidance of magnetic chemotherapy to deep targets, to volumes, and to allow sweeping.

Vasculature geometry and blood flow varies from patient to patient and, with the possible exception of major vessels visualized by MRI, will not be known in a clinical setting. The goal is therefore to use applied (thus known) magnetic fields to manipulate the ferrofluid and, as unknown blood forces disturb it, to continuously put it back to the deep tumor (feedback control). Patient-to-patient vascular geometry variation might not prevent this task in the following sense. Normal metabolically active cells are within <100 µm of blood vessels (Saltzman), so the length scale of vasculature connectivity is generally very small compared to the desired focusing length scale (focusing to a deep target centimeters across would be a dramatic achievement). If there is a concentration of ferrofluid to the right of the target, and a magnetic force is applied to move it left, there should be enough vasculature connectivity to allow the ferrofluid to find a path from right to left. When the vasculature connectivity is interrupted, the control algorithm will see that the fluid is not moving back to its target, and will take corrective actions to circumvent obstructions.

Figure 10:
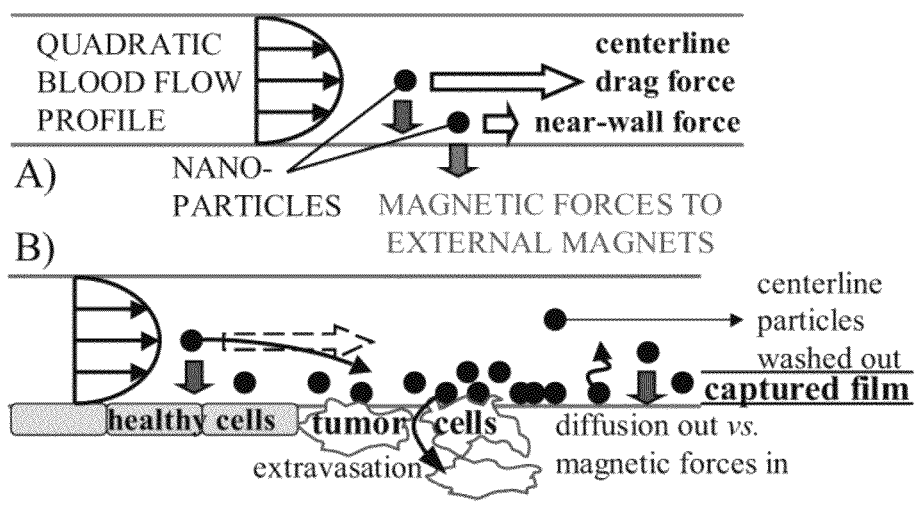
FIG. 10, Panels A-B show the magnetic and blood drag forces on nano-particles. Panel A shows the quadratic flow profile in a blood vessel creates large drag forces on particles at the centerline but only small forces on particles near the vessel wall. Panel B shows that nano-particle capture will occur in a thin film at vessel walls but the thickness of the film will depend on the blood flow velocity and the strength of the magnetic field gradient (in small capillaries the blood flow profile shape is more blunted). In blood-cell diameter microcapillaries where red blood cells pass through in single file, a blood flow "velocity profile" is not defined.

The issue of sufficient magnetic forces versus blood convection forces is subtle. Blood drag flow forces vary with particle position in the blood vessel: a particle at the vessel center-line will see a high velocity and hence high drag force, but a particle near the blood vessel wall will see a near zero velocity (due to the no-slip boundary condition at the wall) and can be held by a small magnetic force (FIG. 10). Trapping of a particle in a blood vessel occurs if the magnetic field pulls the particle out of the strong center-line flow before it leaves the vessel (Voltairas, P A et al. (2002) Journal of Biomechanics 35: 813-821; Mikkelsen, C I (2005) "*Magnetic Separation And Hydrodynamic Interactions In Microfluidic Systems*," Ph.D. Thesis, Department of Micro and Nanotechnology; Lyngby, Denmark: Technical University of Denmark). Thus, when nano-particles are trapped, they are likely confined in thin films at the inside boundaries of blood vessels, which is exactly where they must be to subsequently be taken up by surrounding tissue. It is these thin films of nano particles that we must continuously put back to deep tumor locations by dynamic control.

Initial calculations show that, using MRI-strength magnets, there should be sufficient force to actuate nano-particles, even at 20-30 cm depths. In humans, blood flow velocities range from >1 m/s highest peak velocity in the ascending aorta to ~30 cm/s in main blood return arteries to <5 mm/s in arterioles and venules (Voltairas et al.; Grief et al.; Saltzman; Ganguly, R. et al. (2005) J. of Magnetism and Magnetic Materials 289:331-334). Magnetic forces will not capture particles against the high flow rates in major arteries, instead, focusing will have to be carried out by thin films moving along secondary blood vessels (as does happen in animals and humans for successful focusing to shallow targets). Computing the distance from the vessel wall in a quadratic flow profile where blood drag-flow forces can first overcome the applied magnetic force and wash away the particles, for a 4 Tesla magnet and accounting for particle magnetic saturation, a ferrofluid film of a micrometer to a few hundred nanometer thickness should form in capillaries 20 cm to 30 cm deep. Particle chaining and agglomeration, to the degree that they may occur in-vivo, may also increase forces by allowing magnetic forces to act on particles in small groups.

Deep in-vivo real-time ferrofluid sensing for feedback control can be achieved by making the particles slightly radioactive (see U.S. Pat. Pub. No. 2005/0019257), so that their position can be detected by next-generation gamma cameras or by PET imaging. The radiation dose absorbed by the body during such nuclear imaging is small, far less than an x-ray. CMOS gamma cameras for high-speed imaging are being developed by Westbrook (Parker, S I et al. (2006) IEEE Transactions on Nuclear Science 53:1676-1688; Kenney, C J et al. (2006) Nuclear Instruments and Methods in Physics Research A 565:272-277). These cameras function at >10 kHz (far in excess of speeds needed to combat the ~1 Hz heart-rate blood-flow disturbances in humans), their pixels can be tilted and tiled without gaps, and can be batch fabricated at reasonable cost. It is possible to coat the inside of a sphere or tube with these pixels to form a gamma "camera" that would have near complete solid angle viewing (except for obstructions). Initial calculation show that such cameras are able to detect magnetic nano-particles at concentrations used in human trials (Lubbe et al.; Lemke et al.). Or, as pointed out by Martel (Martel, S. et al. (2007) Applied Physics Letters 90:114105; Mathieu, J B et al. (2007) Biomedical Microdevices 9:801-808), magnetic fields can be duty cycled to both actuate (control mode) and sense (MRI mode) but this leads to a loss in control effectiveness since part of each cycle is devoted to sensing.

Unless magnets or magnetic materials are surgically implanted in patients, which is undesirable and often not clinically feasible, magnetic drug delivery is presently limited to shallow targets (typically <5 cm depth with the strongest possible, still safe, magnetic fields). The control of magnets is provided by the present embodiments permits direction of magnetic carriers to deep tissue volumes. Based on the above-described first-principles magneto-statics and ferrofluid transport model, it has been demonstrated that a sequence of actuations can drive ferrofluid always through a center region thus containing the ferrofluid at the target volume.

In sum, the embodiments described herein demonstrate that magnetic drug delivery is able to target therapy to specific regions in the body, improving efficacy and reducing side effects for treatment of cancer, stroke, infection, and other diseases. Using stationary external magnets, which attract the magnetic drug carriers, this treatment has been limited to shallow targets (<5 cm below skin depth using the strongest possible, still safe, practical magnetic fields). The results presented for the dynamic magnetic actuation indicate that it is possible to vary magnets one against the other to focus carriers between them on average.

EXAMPLE 6

Containment of Magnetic Carriers in a Target Volume

Many patients present to the clinic with widely metastatic cancer, consisting of hundreds to thousands of tumors that vary in size from grossly visible lesions to small microscopic foci. As a practical matter, not all of the tumors can be treated surgically or even by focused radiation therapy. Thus, one approach to the management of patients with this dire diagnosis is to focus on treating the subset of tumors that are the most clinically important, the ones that cause symptoms (morbidity) and death (mortality) if left untreated. In many cancers (for example, breast cancer, prostate cancer) the clinically significant tumor burden is typically present in specific regions of the body. Thus, for example, the target volume for breast cancer is the upper torso and head, because the primary areas of metastasis are the lungs, liver and brain, and the target volume for prostate cancer is the posterior torso and hips, because the primary areas of metastasis are the spine and hips. This is depicted in FIG. 11.

The ability to focus chemotherapy to the anatomical region that contains the significant tumor is clinically important—it will treat the main burden that causes morbidity and mortality but it will spare the rest of the body (bone marrow, immune system, skin and gut cells, and brain cells in the rest of the patient). An ability to confine chemotherapy to an anatomical region through magnetic drug targeting will effectively treat all metastatic foci in that region (without needing to know the precise anatomical locations of the tumors), and is more practical than attempting to perform discrete focusing to each specific tumor, which could number in the thousands, many of which are microscopic and not visible on conventional imaging scans.

For treatment of a patient with metastatic cancer, a target volume is selected based on a known clinical profile for that cancer. For example, if the patient has breast cancer, the target volume is designed to be the upper torso. Magnetizable nanoparticles are designed to incorporate chemotherapeutic agents, and introduced into the patient, by injection for example. Magnetic fields are applied to confine a plurality of the nanoparticles in the target volume.

EXAMPLE 7

Movement of Magnetic Carriers through a Target Volume

It has been discovered by the inventors and their colleagues via autopsies performed on patients with metastasized cancer, that many metastatic tumors are poorly vascularized and have little blood flow to them. This means these metastases are largely isolated from drugs injected systemically into the blood stream and has thus motivated the need for development of the sweep methods and systems proposed in this application. This is depicted in FIG. 12, which shows poorly vascularized metastases 120 in a patient liver 110. A plurality of magnetizable nanoparticles 70 are present throughout the liver 110, and may be transported, for example, via the vascular system 112 in the liver 110.

Using the methods of the present embodiments, in one embodiment magnetizable nanoparticles are introduced into the bloodstream of the patient, and pass through normal vascular circulation and by diffusion into the target volume surrounding the metastatic tumors. Magnetic fields are then applied to sweep the particles a short distance to and through all the metastases. This sweeping movement ensures that the particles are moved through the target volume and pass through all, or the majority of, the metastatic tumors. In between the movements, the magnetic field may be turned off so that the particles can reaccumulate around the tumors. The field is then applied to move the particles in another direction through all the metastases. In this embodiment shaping of the magnetic field in time, space, or both, is used to both direct ferrofluid to the first volume (regional targeting) and then to sweep it into the second volume containing the poorly vascularized metastases (sweeping). In another embodiment the magnetic field is used to direct magnetizable objects to a first volume or volumes that are near, surround, or are otherwise in contact with the metastases in the second volume, and then non-magnetic means move the ferrofluid from the first volume to the second. In this embodiment magnetic control is used for the first step only. In a third embodiment, the ferrofluid accumulates in the first volume by non-magnetic means (e.g. by the usual blood flow, by diffusion, or by sequestering in the liver) and then the magnetic field is used to sweep ferrofluid from the first volume to the many metastases. Exact knowledge of the location, size, and properties of the metastases is not required for this sweep method to be effective. The sweep method has the advantage that it treats all, or the majority of the metastases simultaneously, thus not requiring an impractical and unfeasible one-by-one treatment of thousands of metastatic tumors.

All publications and patents mentioned in this specification are herein incorporated by reference to the same extent as if each was specifically and individually indicated to be incorporated by reference in its entirety. While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth.

What is claimed is:

1. A method for treating a patient comprising the steps of:
   administering a plurality of magnetizable objects to a patient;
   externally applying to the patient a static magnetic field, said field being formed by at least one external magnet;
   altering an arrangement of said field relative to the patient to drive different portions of said plurality of magnetizable objects in different coordinate planes through desired target volumes within the patient.

2. The method of claim 1, wherein at least a portion of said desired target volumes comprise diseased tissue associated with a cancer, a disease of the vascular system, a disease of an organ, an infection, or non-cancerous disease material.

3. The method of claim 2, wherein said diseased tissue is associated with metastasized cancer.

4. The method of claim 2, wherein said diseased tissue contains at least one primary tumor, at least one metastatic tumor, at least one infectious lesion, at least one infectious organism, at least one blood clot, or at least one diseased biological structure.

5. The method of claim 2, wherein said desired target volumes contain at least one individual organ, an organ system, or a specific anatomic region.

6. The method of claim 5, wherein the organ system is selected from the group consisting of the circulatory system, the gastrointestinal tract, the genitourinary tract, the pulmonary system, and the dermal system.

7. The method of claim 4, wherein said diseased tissue contains multiple metastatic tumors or tumor cells.

8. The method of claim 4, wherein said diseased tissue [t] contains multiple infectious lesions, multiple infectious organisms, multiple blood clots, or multiple diseased biological structures.

9. The method of claim 8, wherein said [t] desired target volumes are selected based on the anatomical region in which the multiple infectious lesions, multiple infectious organisms, multiple blood clots, or the multiple diseased biological structures are located.

10. The method of claim 1, wherein said [t] desired target volumes contain multiple clinically significant metastases.

11. The method of claim 1, wherein at least a portion of the desired target volumes is located at least 5 centimeters inside the patient.

12. The method of claim 1, wherein said plurality of magnetizable objects are between about 1 µm and 1 mm in diameter.

13. The method of claim 1, wherein said plurality of magnetizable objects comprises a magnetizable component of a ferrofluid.

14. The method of claim 1, wherein said plurality of magnetizable objects comprise a therapeutic agent, a diagnostic agent, a prophylactic agent, or a detectable label.

15. A method for treating a patient comprising the steps of:
administering a plurality of magnetizable objects to a patient;
directing the plurality of magnetizable objects to a first desired target volume within the patient; and
directing the plurality of magnetizable objects to a second desired target volume within the patient,
wherein said directing steps comprise externally applying a static magnetic field to the patient and altering an arrangement of said field relative to the patient to drive said plurality of magnetizable objects from said first desired target volume to said second desired target volume within the patient.

16. The method of claim 15, further comprising the step of causing the plurality of magnetizable objects to move from the second desired target volume back to the first desired target volume.

17. The method of claim 15, further comprising the step of causing the plurality of magnetizable objects to move from the second desired target volume to a third desired target volume.

18. The method of claim 1, wherein said field is formed by two or more external magnets, wherein said desired target volumes are disposed in an area between said two or more external magnets.

19. The method of claim 1, wherein said arrangement of said field is altered by reorienting said at least one external magnet relative to the patient.

20. The method of claim 1, wherein said arrangement of said field is altered by reorienting the patient relative to said at least one external magnet.

21. A method for treating multiple diseased target volumes within a patient comprising the steps of:
administering a plurality of magnetizable objects to a patient;
externally applying to the patient a magnetic field, said field being formed by at least one external magnet;
confining a first portion of said plurality of magnetizable objects to a first diseased target volume within the patient;
confining a second portion of said plurality of magnetizable objects to a second diseased target volume within the patient, said second diseased target volume discrete from said first diseased target volume; and
treating said first and second diseased target volumes.

22. The method of claim 21, wherein said field is formed by two or more external magnets, wherein said first and second diseased target volumes are disposed in an area between said two or more external magnets.

23. The method of claim 21, wherein each of said first and second diseased target volumes comprises cancerous tissue, an infectious lesion, an infectious organism, or a blood clot.

24. The method of claim 21, wherein said plurality of magnetizable objects comprise a therapeutic agent, a diagnostic agent, a prophylactic agent, or a detectable label.

25. The method of claim 21, wherein said first portion of said plurality of magnetizable objects are confined to said first diseased target volume by a first external magnet, and said second portion of said plurality of magnetizable objects are confined to said second diseased target volume by a second external magnet.

26. The method of claim 21, wherein said first diseased target volume is located in a first portion of an organ or an organ system, and said second diseased target volume is located in a second portion of said organ or said organ system.

* * * * *